United States Patent [19]
Miyanohara et al.

[11] Patent Number: 5,739,018
[45] Date of Patent: Apr. 14, 1998

[54] PACKAGING CELL LINES FOR PSEUDOTYPED RETROVIRAL VECTORS

[75] Inventors: Atsushi Miyanohara, San Diego; Jiing-Kuan Yee, Del Mar; Shin-Tai Chen; Charles Edward Prussak, both of San Diego; Theodore Friedmann, La Jolla, all of Calif.

[73] Assignees: The Regents of the University of California, Oakland; City of Hope, Duarte, both of Calif.

[21] Appl. No.: 694,652

[22] Filed: Aug. 7, 1996

[51] Int. Cl.$^6$ .............................. C12N 5/10; C12N 15/63; C12N 15/86
[52] U.S. Cl. .................. 435/172.3; 435/320.1; 435/325
[58] Field of Search .................. 435/325, 320.1, 435/172.3

[56] References Cited

U.S. PATENT DOCUMENTS

| | | | |
|---|---|---|---|
| 4,861,719 | 8/1989 | Miller | 435/236 |
| 5,464,758 | 11/1995 | Gossen et al. | 435/69.1 |
| 5,512,421 | 4/1996 | Burns et al. | 435/320.1 |

FOREIGN PATENT DOCUMENTS

| | | |
|---|---|---|
| WO 92/05266 | 4/1992 | WIPO . |
| WO 92/14829 | 9/1992 | WIPO . |
| WO 95/34639 | 12/1995 | WIPO . |
| WO 96/35454 | 11/1996 | WIPO . |

OTHER PUBLICATIONS

Yang, Y., et al., "Inducible, High-level Production of Infectious Murine Leukemia Retroviral Vector Particles Pseudotyped With Vesicular Stomatitis Virus G Envelope Protein," *Human Gene Therapy* (1995) 6:1203–1213.

Anderson, W.F., "Human Gene Therapy," *Science* (1992) 256:808–813.

Burns, J.C., et al., "Vesicular Stomatitis Virus G Glycoprotein Pseudotyped Retroviral Vectors: Concentration to Very High Titer and Efficient Gene Transfer Into Mammalian and Nonmammalian Cells," *Proc. Natl. Acad. Sci. USA* (1993) 90:8033–8037.

Byrne, G.W., and Ruddle, F.H., "Multiplex Gene Regulation: A Two-tiered Approach to Transgene Regulation in Transgenic Mice," *Proc. Natl. Acad. Sci. USA* (1989) 86:5473–5477.

Connor, L.M., et al., "Twenty-one Base Pair Repeat Elements Influence the Ability of a Gal4–Tax Fusion Protein to Transactivate the HTLV–I Long Terminal Repeat," *Virol.* (1993) 195:569–577.

Conti, C., et al., "Characterization of Rat Brain Cellular Membrane Components Acting as Receptors for Vesicular Stomatitis Virus," *Arch. Virol.* (1988) 99:261–269.

Crystal, R.G., "Transfer of Genes to Humans: Early Lessons and Obstacles to Success," *Science* (1995) 270:404–410.

Eilers, M., et al., "Chimaeras of Myc Oncoprotein and Steroid Receptors Cause Hormone–dependent Transformation of Cells," *Nature* (1989) 340:66–68.

Emi, N., et al., "Pseudotype Formation of Murine Leukemia Virus With the G Protein of Vesicular Stomatitis Virus," *J. Virol.* (1991) 65(3):1202–1207.

Furth, P.A., "Temporal Control of Gene Expression in Transgenic Mice by a Tetracycline-responsive Promoter," *Proc. Natl. Acad. Sci. USA* (1994) 91:9302–9306.

Gill, G., and Ptashne, M., "Negative Effect of the Transcriptional Activator GAL4," *Nature* (1988) 334:721–724.

Gossen, M., and Bujard, H., "Tight Control of Gene Expression in Mammalian Cells by Tetracycline-responsive Promoters," *Proc. Natl. Acad. Sci. USA* (1992) 89:5547–5551.

Gritz, L., and Davies, J., "Plasmid–encoded Hygromycin B Resistance: The Sequence of Hygromycin B Phosphotransferase Gene and Its Expression in *Escherichia coli* and *Saccharomyces cerevisiae,*" *Gene* (1983) 25:179–188.

Grosveld, F., et al., "Position–independent, High–level Expression of the Human β–globin Gene in Transgenic Mice," *Cell* (1987) 51:975–985.

Hillen, W., and Wissmann, A., "Tet Repressor–tet Operator Interaction," *Protein–Nucleic Acid Interaction*, Topics in Molecular and Structural Biology, Saenger and Heinemann (eds.) Macmillan, London, (1989) 10:143–162.

Hopkins, N., "High Titers of Retrovirus (Vesicular Stomatitis Virus) Pseudotypes, At Last," *Proc. Natl. Acad. Sci. USA* (1993) 90:8759–8760.

Howe, J.R., et al., "The Responsiveness of a Tetracycline–sensitive Expression System Differs in Different Cell Lines," *J. Biol. Chem.* (1995) 270(23):14168–14174.

Kavanaugh, M.P., et al., "Cell–surface Receptors for Gibbon Ape Leukemia Virus and Amphotropic Murine Retrovirus Are Inducible Sodium–dependent Phosphate Symporters," *Proc. Natl. Acad. Sci. USA* (1994) 91:7071–7075.

(List continued on next page.)

*Primary Examiner*—George C. Elliott
*Assistant Examiner*—Johnny F. Railey, II
*Attorney, Agent, or Firm*—Carol L. Francis; Bozicevic & Reed LLP

[57] ABSTRACT

The present invention features packaging cell lines and recombinant retroviral particles produced thereby, particularly pseudotyped retroviral particles. Preferably, the packaging cell lines are derived from HeLa, Cf2Th, D17, MDCK, or BHK cells, most preferably from Cf2Th cells. Retroviral particles are produced by inducibly expressing an envelope protein of interest (e.g., a retroviral envelope or the envelope protein of vesicular stomatitis virus (VSV G)). Inducible expression of the envelope protein is accomplished by operably linking an envelope protein-encoding nucleotide sequence to an inducible promoter (e.g., a promoter composed of a minimal promoter linked to multiple copies of tetO, the binding site for the tetracycline repressor (tetR) of the *Escherichia coli*, tetracycline resistance operon Tn10). Expression from the inducible promoter is regulated by a multi-chimeric transactivating factor, composed of a first ligand-binding domain that negatively regulates transcription from the inducible promoter (e.g., a prokaryotic tetracycline repressor polypeptide (tetR)), a transcriptional activation domain, and a second ligand-binding domain (e.g., a ligand-binding domain of a steroid receptor, preferably an estrogen receptor (ER)).

16 Claims, 20 Drawing Sheets

OTHER PUBLICATIONS

Kessel, M., and Gruss, P., "Murine Developmental Control Genes," *Science* (1990) 249:374–379.

Kumar, V., et al., "Localisation of the Oestradiol–binding and Putative DNA–binding Domains of the Human Oestrogen Receptor," *EMBO J.* (1986) 5(9):2231–2236.

Lin, S., et al., "Integration and Germ–line Tranmission of a Pseudotyped Retroviral Vector in Zebrafish," *Science* (1994) 265:666–669.

Mader, S., and White, J., "A Steroid–inducible Promoter for the Controlled Overexpression of Cloned Genes in Eukaryotic Cells," *Proc. Natl. Acad. Sci. USA* (1993) 90:5603–5607.

Mattioni, T., et al., "Regulation of Protein Activities by Fusion to Steroid Binding Domains," *Methods in Cell Biology* (1994) Chapter 16, 43:335–352.

Mayo, K.E., et al., "The Mouse Metallothionein–I Gene is Transcriptionally Regulated by Cadmium Following Transfection Into Human or Mouse Cells," *Cell* (1982) 29:99–108.

Miller, A.D., "Human Gene Therapy Comes of Age," *Nature*, (1992) 357:455–460.

Miller, A.D., "Retroviral Vectors," *Curr. Top. Microbiol. Immunol.* (1992) 158:1–24.

Miyanohara, A., et al., "Efficient Expression of Retroviral Vector–transduced Human Low Density Lipoprotein (LDL) Receptor in LDL Receptor–deficient Rabbit Fibroblasts in vitro," *Proc. Natl. Acad. Sci. USA* (1988) 85:6538–6542.

Mulligan, R.C., "The Basic Science of Gene Therapy," *Science* (1993) 260:926–932.

Paul, et al., "Increased Viral Titer Through Concentration of Viral Harvests From Retroviral Packaging Lines," *Human Gene Therapy* (1993) 4:609–615.

Picard, D., et al., "A Movable and Regulable Inactivation Function Within the Steroid Binding Domain of the Glucocorticoid Receptor," *Cell* (1988) 54:1073–1080.

Picard, D., "Steroid–binding Domains for Regulating the Functions of Heterologous Proteins in cis," *Trends Cell Biol.* (1993) 3:278–280.

Postle et al., "Nucleotide Sequence of the Repressor Gene of the TN10 Tetracycline Resistance Determinant," *Nucl. Acids Res.* (1984) 12(12):4849–4863.

Pratt, W.B., "Interaction of hsp90 With Steroid Receptors: Organizing Some Diverse Observations and Presenting the Newest Concepts," *Mol. Cell. Endocrinol.* (1990) 74:C69–C76.

Ptashne, M., and Gann, A., "Activators and Targets," *Nature* (1990) 346:329–331.

Resnitzky, D., et al., "Acceleration of the $G_1$/S Phase Transition by Expression of Cyclins D1 and E With an Inducible System," *Mol. Cell Biol.* (1994) 14(3):1669–1679.

Roman et al., "Circulating Human or Canine Factor IX From Retrovirally Transduced Primary Myoblasts and Established Myoblast Cell Lines Grafted Into Murine Skeletal Muscle," *Somat. Cell Genet.* (1992) 18(3):247–258.

Rose, J.K., and Bergmann, J.E., "Expression From Cloned cDNA of Cell–surface Secreted Forms of the Glycoprotein of Vesicular Stomatitis Virus in Eucaryotic Cells," *Cell* (1982) 30:753–762.

Shockett, P., et al., "A Modified Tetracycline–regulated System Provides Autoregulatory, Inducible Gene Expression in Cultured Cells and Transgenic Mice," *Proc. Natl. Acad. Sci. USA* (1995) 92:6522–6526.

Smith, D.F., and Toft, D.O., "Steroid Receptors and Their Associated Proteins," *Mol. Endocrinol.*, (1993) 7(1):4–11.

Takahashi, M., "Kinetic and Equilibrium Characterization of the Tet Repressor–Tetracycline Complex by Fluorescence Measurements," *J. Mol. Biol.* (1986) 187:341–348.

Tovar, K., et al., "Identification and Nucleotide Sequence of the Class E tet Regulatory Elements and Operator and Inducer Binding of the Encoded Purified Tet Repressor," *Mol. Gen. Genet.* (1988) 215:76–80.

Triezenberg, S.J., et al., "Functional Dissection of VP16, the trans–activator of Herpes Simplex Virus Immediate Early Gene Expression," *Gene Dev.* (1988) 2:718–729.

Unger, B., et al., "Nucleotide Sequence of the Gene, Protein Purification and Characterization of the pSC101–encoded Tetracycline Resistance–gene–repressor," *Gene* (1984) 31:103–108.

Unger B., et al., "Nucleotide Sequence of the Repressor Gene of the RA1 Tetracycline Resistance Determinant: Structural and Functional Comparison With Three Related Tet Repressor Genes," *Nucl. Acids Res.* (1984) 12(20):7693–7703.

Wang, Y., et al., "A Regulatory System for Use in Gene Transfer," *Proc. Natl. Acad. Sci. USA* (1994) 91:8180–8184.

Waters, S.H., et al., "The Tetracycline Resistance Determinants of RP1 and Tn1721: Nucleotide Sequence Analysis," *Nucl. Acids Res.* (1983) 11(17):6089–6105.

Wilde, R.J., et al., "Control of Gene Expression in Plant Cells Using a 434:VP16 Chimeric Protein," *Plant Mol. Biol.* (1994) 24:381–388.

Yee, J.–K., "A Liver–specific Enhancer in the Core Promoter Region of Human Hepatitis B Virus," *Science* (1989) 246:658–661.

Yee, J.–K., et al., "A General Method for the Generation of High–titer, Pantropic Retroviral Vectors: Highly Efficient Infection of Primary Hepatocytes," *Proc. Natl. Acad. Sci. USA* (1994) 91:9564–9568.

Yin, M.J., et al., "Chimeric Proteins Composed of Jun and CREB Define Domains Required for Interaction With the Human T–Cell Leukemia Virus Type 1 Tax Protein," *J. Vriol.* (1995) 69(10):62009–6218.

Ory, D.S., et al., 1996, "A stable human–derived packaging cell line for production of high titer retrovirus/vesicular stomatitis virus G pseudotypes," *Proc. Natl. Acad. Sci. USA* 93:11400–6.

| | |
|---|---|
| -GAG POL- | GENES ENCODING MoMLV gag AND pol PROTEINS |
| ▧—GENE—▧ | THE GENOME OF THE RETROVIRAL VECTOR |
| ⊙ | NON-INFECTIOUS RETROVIRAL VIRION |
| CAP———(A)n | THE GENOMIC RNA ENCODED BY THE RETROVIRAL VECTOR VSV G PROTEIN |
| ○ | VSV-G PSEUDOTYPED RETROVIRAL VIRION |

☐ : ESTROGEN RECEPTOR (PAT DOMAIN)
▯ : VP16 (TAD DOMAIN)
○ : TETRACYCLINE REPRESSOR (NAT DOMAIN)
■ : TETRACYCLINE (NAT LIGAND)

FIG. 4A-1

Sequence Range: 1 to 1956

```
         10        20        30        40        50        60
          *         *         *         *         *         *
ATGTCTAGATTAGATAAAAGTAAAGTGATTAACAGCGCATTAGAGCTGCTTAATGAGGTC
 M  S  R  L  D  K  S  K  V  I  N  S  A  L  E  L  L  N  E  V>

70        80        90       100       110       120
          *         *         *         *         *         *
GGAATCGAAGGTTTAACAACCCGTAAACTCGCCCAGAAGCTAGGTGTAGAGCAGCCTACA
 G  I  E  G  L  T  T  R  K  L  A  Q  K  L  G  V  E  Q  P  T>

130       140       150       160       170       180
          *         *         *         *         *         *
TTGTATTGGCATGTAAAAAATAAGCGGGCTTTGCTCGACGCCTTAGCCATTGAGATGTTA
 L  Y  W  H  V  K  N  K  R  A  L  L  D  A  L  A  I  E  M  L>

190       200       210       220       230       240
          *         *         *         *         *         *
GATAGGCACCATACTCACTTTTGCCCTTTAGAAGGGGAAAGCTGGCAAGATTTTTTACGT
 D  R  H  H  T  H  F  C  P  L  E  G  E  S  W  Q  D  F  L  R>

250       260       270       280       290       300
          *         *         *         *         *         *
AATAAGGCTAAAAGTTTTAGATGTGCTTTACTAAGTCATCGCGATGGAGCAAAAGTACAT
 N  K  A  K  S  F  R  C  A  L  L  S  H  R  D  G  A  K  V  H>

310       320       330       340       350       360
          *         *         *         *         *         *
TTAGGTACACGGCCTACAGAAAAACAGTATGAAACTCTCGAAAATCAATTAGCCTTTTTA
 L  G  T  R  P  T  E  K  Q  Y  E  T  L  E  N  Q  L  A  F  L>

370       380       390       400       410       420
          *         *         *         *         *         *
TGCCAACAAGGTTTTTCACTAGAGAATGCATTATATGCACTCAGCGCTGTGGGGCATTTT
 C  Q  Q  G  F  S  L  E  N  A  L  Y  A  L  S  A  V  G  H  F>

430       440       450       460       470       480
          *         *         *         *         *         *
ACTTTAGGTTGCGTATTGGAAGATCAAGAGCATCAAGTCGCTAAAGAAGAAAGGGAAACA
 T  L  G  C  V  L  E  D  Q  E  H  Q  V  A  K  E  E  R  E  T>

490       500       510       520       530       540
          *         *         *         *         *         *
CCTACTACTGATAGTATGCCGCCATTATTACGACAAGCTATCGAATTATTTGATCACCAA
 P  T  T  D  S  M  P  P  L  L  R  Q  A  I  E  L  F  D  H  Q>
```

FIG. 4A-2

```
         550       560       570       580       590       600
          *         *         *         *         *         *
GGTGCAGAGCCAGCCTTCTTATTCGGCCTTGAATTGATCATATGCGGATTAGAAAAACAA
  G  A  E  P  A  F  L  F  G  L  E  L  I  I  C  G  L  E  K  Q>

610       620       630       640       650       660
          *         *         *         *         *         *
CTTAAATGTGAAAGTGGGTCCGCGTACAGCCGCGCGCGTACGAAAAACAATTACGGGTCT
  L  K  C  E  S  G  S  A  Y  S  R  A  R  T  K  N  N  Y  G  S>

670       680       690       700       710       720
          *         *         *         *         *         *
ACCATCGAGGGCCTGCTCGATCTCCCGGACGACGACGCCCCCGAAGAGGCGGGGCTGGCG
  T  I  E  G  L  L  D  L  P  D  D  D  A  P  E  E  A  G  L  A>

730       740       750       760       770       780
          *         *         *         *         *         *
GCTCCGCGCCTGTCCTTTCTCCCCGCGGGACACACGCGCAGACTGTCGACGGCCCCCCCG
```

FIG. 4B-1

```
         790       800       810       820       830       840
          *         *         *         *         *         *
ACCGATGTCAGCCTGGGGGACGAGCTCCACTTAGACGGCGAGGACGTGGCGATGGCGCAT
 T  D  V  S  L  G  D  E  L  H  L  D  G  E  D  V  A  M  A  H>

850       860       870       880       890       900
          *         *         *         *         *         *
GCCGACGCGCTAGACGATTTCGATCTGGACATGTTGGGGGACGGGGATTCCCCGGGTCCG
 A  D  A  L  D  D  F  D  L  D  M  L  G  D  G  D  S  P  G  P>

910       920       930       940       950       960
          *         *         *         *         *         *
GGATTTACCCCCCACGACTCCGCCCCCTACGGCGCTCTGGATATGGCCGACTTCGAGTTT
 G  F  T  P  H  D  S  A  P  Y  G  A  L  D  M  A  D  F  E  F>

970       980       990      1000      1010      1020
          *         *         *         *         *         *
GAGCAGATGTTTACCGATCCCCTTGGAATTGACGAGTACGGTGGGGATCCATCTGCTGGA
 E  Q  M  F  T  D  P  L  G  I  D  E  Y  G  G  D  P  S  A  G>

1030      1040      1050      1060      1070      1080
          *         *         *         *         *         *
GACATGAGAGCTGCCAACCTTTGGCCAAGCCCGCTCATGATCAAACGCTCTAAGAAGAAC
 D  M  R  A  A  N  L  W  P  S  P  L  M  I  K  R  S  K  K  N>

1090      1100      1110      1120      1130      1140
          *         *         *         *         *         *
AGCCTGGCCTTGTCCCTGACGGCCGACCAGATGGTCAGTGCCTTGTTGGATGCTGAGCCC
 S  L  A  L  S  L  T  A  D  Q  M  V  S  A  L  L  D  A  E  P>

1150      1160      1170      1180      1190      1200
          *         *         *         *         *         *
CCCATACTCTATTCCGAGTATGATCCTACCAGACCCTTCAGTGAAGCTTCGATGATGGGC
 P  I  L  Y  S  E  Y  D  P  T  R  P  F  S  E  A  S  M  M  G>

1210      1220      1230      1240      1250      1260
          *         *         *         *         *         *
TTACTGACCAACCTGGCAGACAGGGAGCTGGTTCACATGATCAACTGGGCGAAGAGGGTG
 L  L  T  N  L  A  D  R  E  L  V  H  M  I  N  W  A  K  R  V>

1270      1280      1290      1300      1310      1320
          *         *         *         *         *         *
CCAGGCTTTGTGGATTTGACCCTCCATGATCAGGTCCACCTTCTAGAATGTGCCTGGCTA
 P  G  F  V  D  L  T  L  H  D  Q  V  H  L  L  E  C  A  W  L>
```

FIG. 4B-2

```
          1330        1340        1350        1360        1370        1380
            *           *           *           *           *           *
       GAGATCCTGATGATTGGTCTCGTCTGGCGCTCCATGGAGCACCCAGTGAAGCTACTGTTT
        E  I  L  M  I  G  L  V  W  R  S  M  E  H  P  V  K  L  L  F>

1390        1400        1410        1420        1430        1440
            *           *           *           *           *           *
       GCTCCTAACTTGCTCTTGGACAGGAACCAGGGAAAATGTGTAGAGGGCATGGTGGAGATC
        A  P  N  L  L  L  D  R  N  Q  G  K  C  V  E  G  M  V  E  I>

1450        1460        1470        1480        1490        1500
            *           *           *           *           *           *
       TTCGACATGCTGCTGGCTACATCATCTCGGTTCCGCATGATGAATCTGCAGGGAGAGGAG
        F  D  M  L  L  A  T  S  S  R  F  R  M  M  N  L  Q  G  E  E>

1510        1520        1530        1540        1550        1560
            *           *           *           *           *           *
       TTTGTGTGCCTCAAATCTATTATTTTGCTTAATTCTGGAGTGTACACATTTCTGTCCAGC
        F  V  C  L  K  S  I  I  L  L  N  S  G  V  Y  T  F  L  S  S>
```

FIG. 4C

```
      1570      1580      1590      1600      1610      1620
        *         *         *         *         *         *
ACCCTGAAGTCTCTGGAAGAGAAGGACCATATCCACCGAGTCCTGGACAAGATCACAGAC
 T  L  K  S  L  E  E  K  D  H  I  H  R  V  L  D  K  I  T  D>

1630      1640      1650      1660      1670      1680
        *         *         *         *         *         *
ACTTTGATCCACCTGATGGCCAAGGCAGGCCTGACCCTGCAGCAGCAGCACCAGCGGCTG
 T  L  I  H  L  M  A  K  A  G  L  T  L  Q  Q  Q  H  Q  R  L>

1690      1700      1710      1720      1730      1740
        *         *         *         *         *         *
GCCCAGCTCCTCCTCATCCTCTCCCACATCAGGCACATGAGTAACAAAGGCATGGAGCAT
 A  Q  L  L  L  I  L  S  H  I  R  H  M  S  N  K  G  M  E  H>

1750      1760      1770      1780      1790      1800
        *         *         *         *         *         *
CTGTACAGCATGAAGTGCAAGAACGTGGTGCCCCTCTATGACCTGCTGCTGGAGATGCTG
 L  Y  S  M  K  C  K  N  V  V  P  L  Y  D  L  L  L  E  M  L>

1810      1820      1830      1840      1850      1860
        *         *         *         *         *         *
GACGCCCACCGCCTACATGCGCCCACTAGCCGTGGAGGGGCATCCGTGGAGGAGACGGAC
 D  A  H  R  L  H  A  P  T  S  R  G  G  A  S  V  E  E  T  D>

1870      1880      1890      1900      1910      1920
        *         *         *         *         *         *
CAAAGCCACTTGGCCACTGCGGGCTCTACTTCATCGCATTCCTTGCAAAAGTATTACATC
 Q  S  H  L  A  T  A  G  S  T  S  S  H  S  L  Q  K  Y  Y  I>

1930      1940      1950
        *         *         *
ACGGGGGAGGCAGAGGGTTTCCCTGCCACAGTCTGA
 T  G  E  A  E  G  F  P  A  T  V  *>
```

FIG. 12
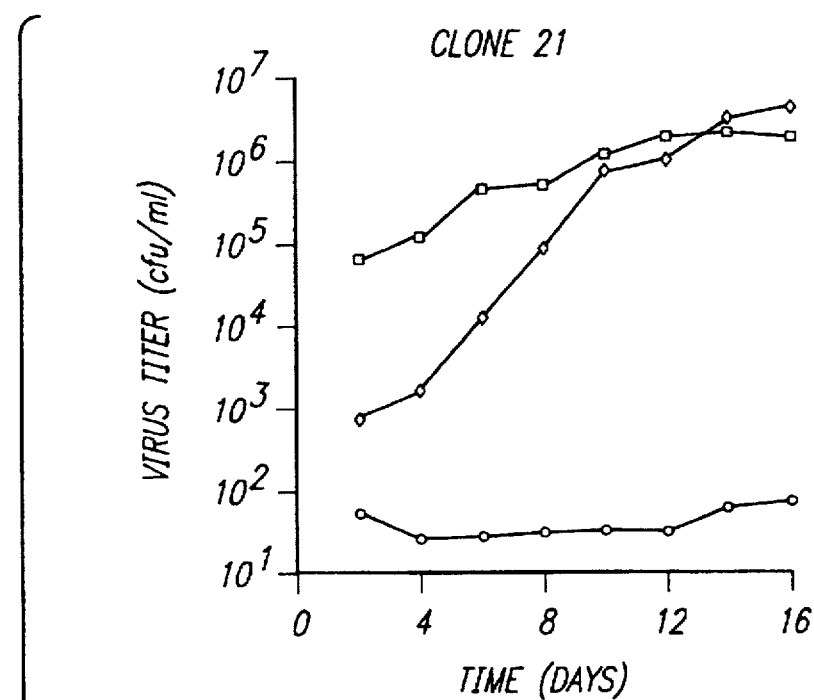
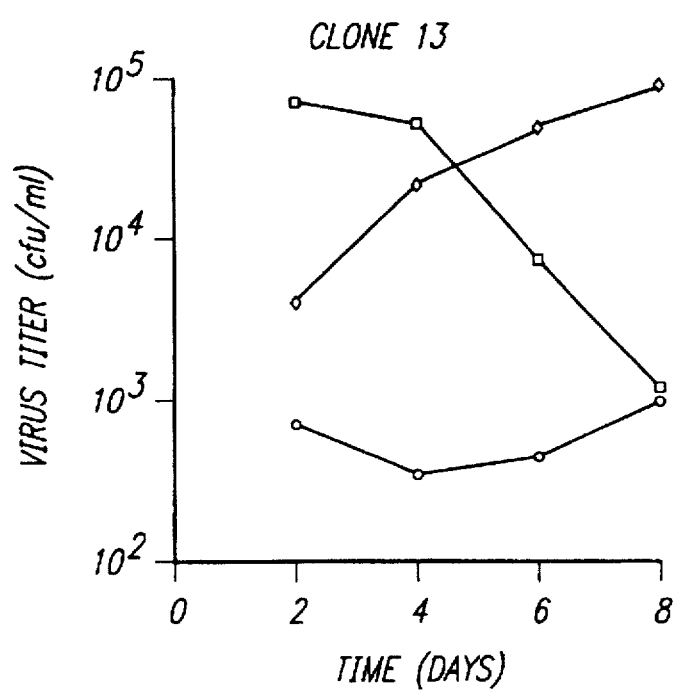

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 481 base pairs
        ( B ) TYPE: nucleic acid
        ( C ) STRANDEDNESS: single (D) TOPOLOGY: linear (xi) SEQUENCE DESCRIPTION: SEQ ID NO:1:

```
CTCGAGTTTA CCACTCCCTA TCAGTGATAG AGAAAAGTGA AAGTCGAGTT TACCACTCCC      60
TATCAGTGAT AGAGAAAAGT GAAAGTCGAG TTTACCACTC CCTATCAGTG ATAGAGAAAA     120
GTGAAAGTCG AGTTTACCAC TCCCTATCAG TGATAGAGAA AAGTGAAAGT CGAGTTTACC     180
ACTCCCTATC AGTGATAGAG AAAAGTGAAA GTCGAGTTTA CCACTCCCTA TCAGTGATAG     240
AGAAAAGTGA AAGTCGAGTT TACCACTCCC TATCAGTGAT AGAGAAAAGT GAAAGTCGAG     300
CTCGGTACCC GGGTCGAGTA GGCGTGTACG GTGGGAGGCC TATATAAGCA GAGCTCGTTT     360
AGTGAACCGT CAGATCGCCT GGAGACGCCA TCCACGCTGT TTTGACCTCC ATAGAAGACA     420
CCGGGACCGA TCCAGCCTCC GCGGCCCCGA ATTCGAGCTC GGTACCCGGG GATCCTCTAG     480
A                                                                    481
```

PACKAGING CELL LINES FOR PSEUDOTYPED RETROVIRAL VECTORS

This invention was made with Government support under Grant Nos. DK49023 and HL53680 awarded by the National Institute of Health. The Government may have certain rights in this invention.

FIELD OF THE INVENTION

This invention relates generally to the field of recombinant retroviral particles for use in gene delivery, e.g., for use in gene therapy.

BACKGROUND OF THE INVENTION

Retroviruses are enveloped RNA viruses that, after infection of a host cell, reverse transcribe their RNA genomes into a DNA intermediate, or provirus. The provirus can be stably integrated into the host's cellular DNA. Gene products encoded by the provirus are then expressed by the host cell to produce retroviral virions, thereby replicating the virus. Because the retroviral genome can be manipulated to include exogenous nucleotide sequence(s) of interest for expression in a target cell, retroviral vectors are important tools for stable gene transfer into mammalian cells. Many proposed gene therapy applications use retroviral vectors to take advantage of the ability of these naturally infectious agents to transfer and efficiently express recombinant nucleotide sequences in susceptible target cells (see, e.g., Miller 1992 *Nature* 357:455–460; Miller Curt. *Top. Microbiol. Immunol.* 158:1–24). Retroviral vectors suitable for use in such applications are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase).

Use of retroviral vectors is limited in many aspects. For example, although retroviruses can efficiently infect and stably integrate into the genome of rapidly-dividing cells, retrovital integration into the genome of non-dividing or slowly dividing cells is inefficient (Springett et al. 1989 *J. Virol.* 63:3865–3869; Miller et al. 1990 *Mol. Cell. Biol.* 10:4239–4242; Roe et al. 1993 *EMBO J.* 12:2099–2108). Most packaging systems provide only modest vector titers, and the fragility of retroviral vector particles complicate purification and concentration (Paul et al. 1993 *Hum. Gene Therap.* 4:609–615). Finally, retroviruses enter target cells by binding of retroviral envelope glycoproteins (encoded by the env gene) to specific target cell surface receptors. This envelope protein-cell surface receptor interaction is often species specific, and in some cases even tissue specific. Moreover, the level of expression of the cell surface receptor on the target cells can vary widely among target cells. As a result, retroviruses usually have a limited host range (Kavanaugh et al. 1994 *Proc. Natl. Acad. Sci. USA* 91:7071–7075; Hopkins 1993 *Proc. Natl. Acad. Sci. USA* 90:8759–8760).

One strategy for both expanding retroviral host cell range and increasing the structural stability of the retroviral virion involves production of pseudotyped retroviral viral vectors. Pseudotyped retroviral vectors useful in transformation of target cells are generally composed of retroviral virion structural proteins (e.g., Gag proteins), a recombinant RNA genome containing the nucleotide sequence of interest, the Pol protein for reverse transcription of the recombinant RNA contained in the virion, and a non-retroviral envelope protein or an envelope protein from a different retrovirus. The recombinant RNA genome is usually replication defective, e.g., defective in the pol and/or gag genes, to prevent production of infectious retrovirus following transfer of the nucleotide sequence of interest into the target cell. The envelope protein of the pseudotyped retrovirus is normally selected to provide a broader host range or to provide selective targeting of cells to be infected.

The envelope protein of vesicular stomatitis virus (VSV), termed VSV G, is a strong candidate for use in the production of pseudotyped retroviral vectors. VSV G can infect a variety of cell types from a wide range of mammalian and non-mammalian species, including humans, hamsters, insects, fish, and frogs, with a greater efficiency than traditional amphotropic retroviral vectors. The putative receptor(s) for VSV include phosphatidyl serine, phosphatidyl inositol and/or GM3 ganglioside (Mastromarino, et al., 1987 *J. Gen. Virol.* 68:2359–2369; Conti, et al., 1988 *Arch. Virol.* 99:261–269), all of which are ubiquitous and abundant components of plasma membrane. VSV G pseudotyped retroviral vectors have enhanced structural stability allowing for concentration to titers of greater than $10^9$ infectious particles per ml by ultracentrifugation. (Emi et al. 1991 *J. Virol.* 65:1202–1207; Yee et al., 1994 *Proc. Natl. Acad. Sci. USA* 91:9564–9568; Burns et al. 1993 *Proc. Natl. Acad. Sci. USA* 90:8033–8037; Lin et al. 1994 *Science* 265:666–669). When expressed in packaging cells, VSV G efficiently forms pseudotyped virions with the genome and core components derived from retroviruses such as murine leukemia virus (MuLV). Packaging cell lines that express the retroviral gag and pol genes and the VSV G envelope protein produce pseudotyped retroviral particles having the retroviral Gag and Pol proteins enclosed in a VSV G-containing envelope (see FIG. 1), resulting in the production of virions whose infectivity is blocked by anti-VSV G antibodies (Emi et al. 1991 supra; Yee et al. 1994 supra). These properties of VSV G pseudotyped virions not only expand the use of retroviral vectors for genetic studies in previously inaccessible species, but also facilitate more efficient pre-clinical and clinical studies of the potential for human gene therapy.

However, production of VSV G pseudotyped retroviral virions has met with several difficulties. First, VSV G is cytotoxic. High level expression of VSV G in mammalian cells leads to syncytia formation and cell death, making it difficult to establish stable cell lines expressing VSV G (Yee et al. 1994 supra; Burns et al. 1993 supra). Pseudotyped VSV G virions have been produced by transient expression of the VSV G gene after DNA transfection of 293GP cells expressing the Gag and Pol components of MuLV, yielding vector preparations having titers of $10^5$–$10^6$ infectious viral particles per ml (Yee et al 1994 supra). However, generation of VSV G pseudotyped virions by transient VSV G expression is cumbersome, labor intensive, and unlikely to be amenable to clinical applications that demand reproducible, certified vector preparations.

Several inducible promoter systems have been described including those controlled by heavy metals (Mayo et al. 1982 *Cell* 29:99–108), RU-486 (a progesterone antagonist) (Wang et al. 1994 *Proc. Natl. Acad. Sci. USA* 91:8180–8184), steroids (Mader and White, 1993 *Proc. Natl. Acad. Sci. USA* 90:5603–5607), and tetracycline (Gossen and Bujard 1992 *Proc. Natl. Acad. Sci. USA* 89:5547–5551; U.S. Pat. No. 5,464,758). However, heavy metals are toxic to cells, compromising the use of this inducible promoter system. The inducible promoter of the RU-486 system is significantly expressed in the absence of RU-486 and is induced only 10- to 20-fold in the presence of RU-486 (Wang et al. 1994), making this system undesirable for expression of VSV G for production of pseudotyped retroviral virions.

The tetracycline-inducible system of Gossen and Bujard has been used to regulate inducible expression of several genes (Gossen and Bujard 1992, supra; Furth et al. 1994 *Proc. Natl. Acad. Sci. USA* 91:9302–9306; Howe et al. 1995 *J. Biol. Chem.* 270:14168–14174; Resnitzky et al. 1994 *Mol. Cell. Biol.* 14:1669–1679; Shockett et al. 1995 *Proc. Natl. Acad. Sci. USA* 92:6522–6526). This system uses a chimeric transcription factor, termed tTA, which is composed of the repressor of *Escherichia coli*, (*E. coli*) tetracycline-resistance operon (tetR) and the activation domain (carboxyl terminal domain) of virion protein 16 (VP16) of herpes simplex virus (HSV) (Triezenberg et al. 1988 *Genes Dev.* 2:718–729). The gene of interest is placed downstream of a minimal cytomegalovirus (CMV) 1A promoter, derived from the immediate early CMV genes, which is linked to multiple copies of tetO, the binding site for the tetracycline repressor tetR. In the absence of tetracycline, the tetR portion of the transactivator binds the tetO sequences of the promoter and the VP16 portion facilitates transcription. When tetracycline is present, tetracycline binds the tetR portion of tTA, which in turn prevents binding of the tetR portion to the tetO sequence(s) of the promoter, thus inhibiting transcription. Since even low concentrations of tetracycline are sufficient to block tTA function, and since most mammalian cells can tolerate tetracycline, this system provides a tightly regulated on/off switch for gene expression that can be controlled by varying the tetracycline concentration to which the cells are exposed. However, establishment of cell lines stably expressing large amounts of the tetracycline-transactivator (tTA) is difficult, since the VP16 activation domain decreases, or "squelches," general cellular transcription when expressed in large quantities in mammalian cells (Gossen and Bujard 1992 supra Gossen and Bujard 1992, supra; Shockett et al. 1995 supra; Gill et al. 1988 *Nature* 334:721–724; Ptashne et al. 1990 *Nature* 346:329–331). Thus, the tTA inducible expression system is not desirable for production of VSV G pseudotyped retroviral vectors.

There is a clear need in the field for an inducible expression system useful in the production of cytotoxic gene products, such as VSV G, and useful in the production VSV G pseudotyped retroviral vectors.

SUMMARY OF THE INVENTION

The present invention features packaging cell lines and recombinant retroviral particles produced thereby, particularly pseudotyped retroviral particles. Preferably, the packaging cell lines are derived from HeLa, Cf2Th, D17, MDCK, or BHK cells, most preferably from Cf2Th cells. Retroviral particles are produced by inducibly expressing an envelope protein of interest (e.g., a retroviral envelope or the envelope protein of vesicular stomatitis virus (VSV G)). Inducible expression of the envelope protein is accomplished by operably linking an envelope protein-encoding nucleotide sequence to an inducible promoter (e.g., a promoter composed of a minimal promoter linked to multiple copies of tetO, the binding site for the tetracycline repressor (tetR) of the *Escherichia coli*, tetracycline resistance operon Tn10). Expression from the inducible promoter is regulated by a multi-chimeric transactivating factor, composed of a first ligand-binding domain that negatively regulates transcription from the inducible promoter (e.g., a prokaryotic tetracycline repressor polypeptide (tet R)), a transcriptional activation domain, and a second ligand-binding domain (e.g., a ligand-binding of a steroid receptor, preferably an estrogen receptor (ER)). Transcription of the envelope-encoding nucleotide sequence under control of the inducible promoter is activated by the multi-chimeric transactivator when tetracycline is absent.

A primary object of the invention is to provide a packaging cell line that produces retroviral particles, especially pseudotyped retroviral particles, more efficiently (e.g., at higher titers) than conventional packaging cell lines.

Another object of the invention is to provide recombinant retroviral vectors, especially pseudotyped retroviral vectors, that are useful in both in vitro and in vivo transformation of a target cell.

Another advantage of the invention is that packaging cell lines can be produced that contain an envelope-encoding nucleotide sequence stably integrated in the cell's genome, which sequence can be inducibly expressed, thus allowing generation of packaging cell lines capable of expressing an envelope protein that is otherwise toxic to the host cell (e.g., VSV G).

Another advantage of the invention is that the multi-chimeric transactivator can be expressed in a packaging cell at levels sufficient to provide for expression of envelope protein at levels sufficient to provide high titers of pseudotyped retroviral vectors.

Another advantage of the invention is that the packaging cell lines do not have the potential to produce replication competent retroviruses.

Still another advantage of the invention is that packaging cell lines according to the invention that are derived from Cf2Th cells provide significantly higher titers of VSV G pseudotyped retroviral vectors within a given time period than other packaging cell lines.

These and other objects, advantages and features of the present invention will become apparent to those persons skilled in the art upon reading the details of the vectors, cell lines and methodology as more fully set forth below.

BRIEF DESCRIPTION OF THE DRAWINGS

FIG. 4A–4C is a schematic illustrating the nucleotide and amino acid sequences of the multi-chimeric transactivator tTAER.

FIG. 12 is a set of two graphs showing a time course of production of VSV G pseudotyped virus by 293GP/tTAER/G clone 21 and 293GP/tTAER/G clone 13 cells of a period of 16 days and 8 days, respectively. Cells were incubated in DMEM alone (diamond), DMEM plus tetracycline (circle), DMEM plus β-estradiol (square) for the time period indicated. Horizontal and vertical axes measure fluorescence intensity and cell number, respectively.

DESCRIPTION OF THE PREFERRED EMBODIMENTS

Figure 1:
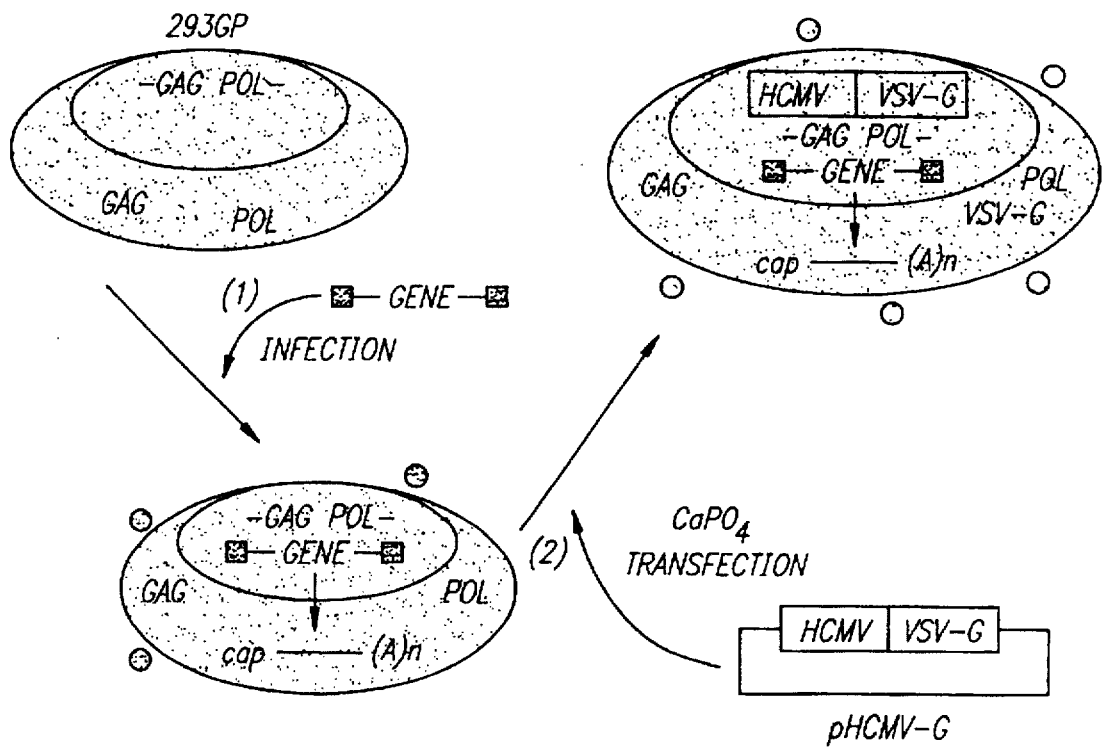
FIG. 1 is a schematic illustration of the general steps in the production of VSV G pseudotyped retroviral vectors. The retroviral vector (■) is used to infect a cell, and a clone having the integrated retroviral vector is selected for subsequent production of VSV G pseudotyped virus. The virions (○) are noninfectious due to the absence of envelope protein on the cell surface. VSV G pseudotyped virus is generated by introducing a VSV G encoding sequence into the clone and transiently expressing VSV G. Infections VSV G pseudotyped virus (●) is collected 24 to 96 hours after transfection.

Before the present inducible expression system, use of the inducible expression system to generate packaging cell lines for retroviral vectors pseudotyped with VSV G, and constructs, vector particles, and packaging cell lines associated therewith are described, it is to be understood that this invention is not limited to the particular methodology, protocols, cell lines, retroviruses, vectors, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a packaging cell" includes a plurality of such cells and reference to "the retroviral vector" includes reference to one or more vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

By "inducible expression system" is meant a construct or combination of constructs that includes a nucleotide sequence encoding a multi-chimeric transactivator, an inducible promoter that can be transcriptionally activated by the multi-chimeric transactivator, and a nucleotide sequence of interest operably linked to the inducible promoter. For example, an exemplary inducible expression system of the invention includes a nucleotide sequence encoding tTAER and a nucleotide sequence of interest operably linked to a inducible promoter composed of a minimal promoter operably linked to at least one tetO sequence.

By "transactivator," "transactivating factor," or "transcriptional activator" is meant a polypeptide that facilitates transcription from a promoter. Where the promoter is an inducible promoter, the transactivator activates transcription in response to a specific transcriptional signal or set of transcriptional signals. For example, in the inducible expression system of the invention, tTAER is a transactivator that facilitates transcription from the inducible tetO promoter when tTAER is not bound to tetracycline.

By "multi-chimeric transactivator" is meant a transactivator composed of a fusion protein derived from at least three different polypeptides. In general, the multi-chimeric transactivators of the invention are composed of: 1) a first ligand-binding domain that, when bound to its ligand, negatively affects transcriptional activation by the multi-chimeric transactivator (NAT domain); 2) a transcriptional activation domain, generally derived from a eukaryotic transcriptional activator; and 3) a second ligand-binding domain (SLB domain). Preferably, the NAT domain is a prokaryotic tetracycline repressor polypeptide and the SLB domain is a ligand binding-domain of a steroid receptor. Preferably, the transcriptional activation domain is the carboxyl terminal domain of virion protein 16 (VP16) of herpes simplex virus (HSV).

By "tTAER" is meant a multi-chimeric transactivator composed of a tetR polypeptide, as activation domain of VP16, and a ligand binding domain of an estrogen receptor.

"Tetracycline repressor protein," tetracycline repressor polypeptide," "tetR polypeptide," and "tetR protein" are used interchangeably herein to mean a polypeptide that exhibits both 1) specific binding to tetracycline and/or tetracycline derivatives; and 2) specific binding to tetO sequences when the tetR polypeptide is not bound by tetracycline or a tetracycline analog(s). "TetR polypeptide" is meant to include a naturally-occurring (i.e., native) tetR polypeptide sequence and functional derivatives thereof.

By "transcriptional activation domain" is meant a polypeptide sequence that facilitates transcriptional activation from a promoter. "Transcriptional activation domain" includes transcriptional activation domains derived from the naturally-occurring amino acid sequence of a transcription factor as well as functional derivatives thereof.

By "ligand-binding domain of a steroid receptor" is meant a polypeptide that exhibits specific binding to a steroid and/or a steroid analog and protects the eukaryotic host cell in which the transactivator is expressed from any cytotoxic effects of the multi-chimeric transactivator (e.g., by regulating function of the transactivator and/or by preventing or reducing cellular transcription associated with the GTA portion of the transactivator). "Ligand-binding domain of a steroid receptor" is meant to include naturally-occurring (i.e., native) steroid receptor ligand-binding domains and functional derivatives thereof.

By "envelope protein" is meant a polypeptide that 1) can be incorporated into an envelope of a retrovirus; and 2) can bind target cells and facilitate infection of the target cell by the RNA virus that it envelops. "Envelope protein" is meant to include naturally-occurring (i.e., native) envelope proteins and functional derivatives thereof that 1) can form pseudotyped retroviral virions according to the invention, and 2) exhibit a desired functional characteristic(s) (e.g., facilitate viral infection of a desired target cell, and/or exhibit a different or additional biological activity). In general, envelope proteins of interest in the invention include any viral envelope protein that can, in combination with a retroviral genome, retroviral Pol, retroviral Gag, and other essential retroviral components, form a retroviral particle. Such envelope proteins include retroviral envelope proteins derived from any suitable retrovirus (e.g., an amphotropic, xenotropic, or polytropic retrovirus) as well as non-retroviral envelope proteins that can form pseudotyped retroviral virions (e.g., VSV G). Envelope proteins of particular interest include, but are not limited to, envelope protein of vesicular stomatis virus (VSV G), HTLV-1, HIV-1, gibbon ape leukemia virus (GALV), Sindai virus, influenza virus, rhabdovirus, and rabies virus.

By "functional derivative of a polypeptide" is meant an amino acid sequence derived from a naturally-occurring polypeptide that is altered relative to the naturally-occurring polypeptide by virtue of addition, deletion, substitution, or other modification of the amino acid sequence. "Functional derivatives" contemplated herein exhibit the characteristics of the naturally-occurring polypeptide essential to the operation of the invention. For example, by "functional derivative of tetR" is meant a polypeptide derived from tetR that retains both 1) tetracycline or tetracycline analog binding and 2) the ability to inhibit transcriptional activation by tTAER when bound to tetracycline or an analog thereof. By "functional derivative of a VP16 transcriptional activation domain" is meant a polypeptide derived from a VP16 transcriptional activation domain that can facilitate transcription from the promoter. By "functional derivative of a ligand-binding domain of a steroid receptor" is meant a polypeptide derived from a ligand-binding domain of a steroid receptor that 1) retains steroid or steroid analog binding, and 2) protects the eukaryotic cell from any cytotoxic effects of the multi-chimeric transactivator (e.g., by regulating function of the transactivator and/or by preventing or reducing general cellular transcription normally associated with tTA). Methods of making functional derivatives (e.g., using recombinant DNA methodologies (e.g., site-specific mutation, fusion protein construction), chemical modifications of amino acid residues, and other techniques) are well known in the art.

By "promoter" is meant a minimal DNA sequence sufficient to direct transcription of a DNA sequence to which it is operably linked. "Promoter" is also meant to encompass those promoter elements sufficient for promoter-dependent gene expression controllable for cell-type specific expression, tissue-specific expression, or inducible by external signals or agents; such elements may be located in the 5' or 3' regions of the naturally-occurring gene.

By "inducible promoter" is meant a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/or affect function of the transcriptional activator itself. For example, the transcriptional activator of the present invention, tTAER, induces transcription from its corresponding inducible promoter when tetracycline is absent, i.e. tetracycline is not bound to tTAER.

By "construct" is meant a recombinant nucleotide sequence, generally a recombinant DNA molecule, that has been generated for the purpose of the expression of a specific nucleotide sequence(s), or is to be used in the construction of other recombinant nucleotide sequences. In general, "construct" is used herein to refer to a recombinant DNA molecule.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by a DNA of interest).

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "target cell" is meant a cell(s) that is to be transformed using the methods and compositions of the invention. Transformation may be designed to non-selectively or selectively transform the target cell(s). In general, target cell as used herein means a eukaryotic cell that can be infected by a VSV G pseudotyped retrovital vector according to the invention.

By "transformed cell" is meant a cell into which (or into an ancestor of which) has been introduced, by means of recombinant DNA techniques, a DNA molecule encoding a gene product (e.g., RNA and/or protein) of interest (e.g., nucleic acid encoding a therapeutic cellular product).

By "nucleotide sequence of interest" or "DNA of interest" is meant any nucleotide or DNA sequence that encodes a protein or other molecule that is desirable for expression in a host cell (e.g., for production of the protein or other biological molecule (e.g., a therapeutic cellular product) in the target cell). The nucleotide sequence of interest is generally operatively linked to other sequences which are needed for its expression, e.g., a promoter. In general, a nucleotide sequence of interest present in the genome of a recombinant retroviral particle of the invention encodes any gene product of interest, usually a therapeutic gene product where the recombinant retroviral particle is to be used to transform cells in vivo (e.g., in a gene therapy application in humans).

By "therapeutic gene product" is meant a polypeptide, RNA molecule or other gene product that, when expressed in a target cell, provides a desired therapeutic effect, e.g., repair of a genetic defect in the target cell genome (e.g., by complementation), expression of a polypeptide having a desired biological activity, and/or expression of an RNA molecule for antisense therapy (e.g., regulation of expression of a endogenous or heterologous gene in the target cell genome).

By "subject" or "patient" is meant any subject for which cell transformation or gene therapy is desired, including humans, cattle, dogs, cats, guinea pigs, rabbits, mice, insects, horses, chickens, and any other genus or species having cells that can be infected with a viral vector having an envelope containing VSV G.

By "transgenic organism" is meant a non-human organism (e.g., single-cell organisms (e.g., yeast), mammal, non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

By "viral vector" is meant a recombinant viral particle that accomplishes transformation of a target cell with a nucleotide sequence of interest.

By "virion," "viral particle," or "retroviral particle" is meant a single virus minimally composed of an RNA genome, Pol protein (for reverse transcription of the RNA genome following infection), Gag protein (structural protein present in the nucleocapsid), and an envelope protein. As used herein, the RNA genome of the retroviral particle is usually a recombinant RNA genome, e.g., contains an RNA sequence exogenous to the native retroviral genome and/or is defective in an endogenous retroviral sequence (e.g., is defective in pol, gag, and/or env, and, as used herein, is normally defective in all three genes).

By "pseudotyped viral particle," or "pseudotyped retroviral particle" is meant a viral particle having an envelope protein that is from a virus other than the virus from which the RNA genome is derived. The envelope protein can be from a retrovirus of a species different from the retrovirus from which the RNA genome is derived or from a non-retroviral virus (e.g., vesicular stomatitis virus (VSV)). Preferably, the envelope protein of the pseudotyped retroviral particle is VSV G.

By "VSV G" or "VSV G envelope protein" is meant the envelope protein of vesicular stomatitis virus (VSV) or a polypeptide derived therefrom or recombinant fusion polypeptide having a VSV G polypeptide sequence fused to a heterologous polypeptide sequence, where the VSV G-derived polypeptide of recombinant fusion polypeptide can be contained in a viral envelope of a pseudotyped retroviral particle and retains infectivity for a desired target cell (e.g., a range of desired eukaryotic cells, or a specific target cell of interest).

By "VSV G pseudotyped virus," "VSV G pseudotyped retrovirus," "VSV G pseudotyped viral particle," or "VSV G pseudotyped retroviral particle," is meant a retrovirus having the envelope protein VSV G, e.g., either in combination with or substantially substituted for the endogenous retroviral envelope. Preferably, VSV G is present in the VSV G pseudotyped viral envelope such that VSV G represents about 50% of the envelope protein(s) present in the envelope, more preferably about 75%, even more preferably about 90% to about 95%, still more preferably greater than about 95%, most preferably about 100% or such that VSV G is substantially the only envelope protein present in the pseudotyped viral particle envelope.

The invention will now be described in further detail.

Overview of the Inducible Expression System of the Invention

Figure 2A:
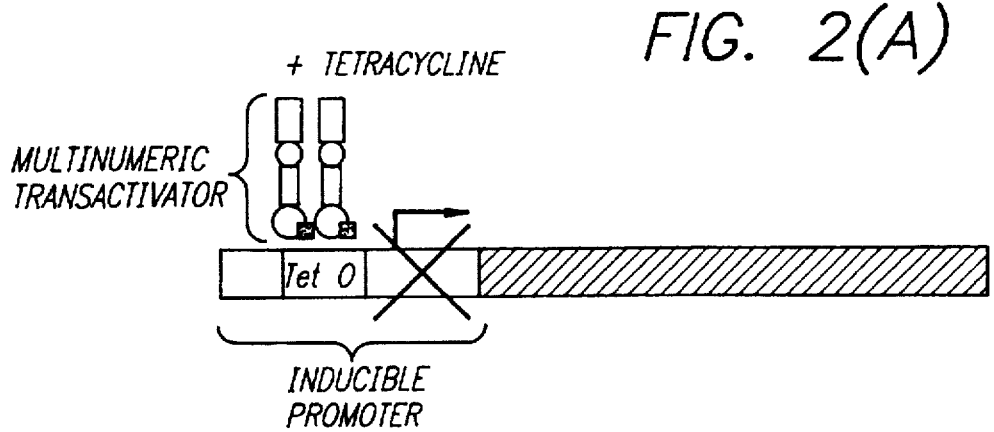
FIGS. 2A, 2B and 2C are schematic illustrations of the inducible expression system of the invention.
Figure 2B:
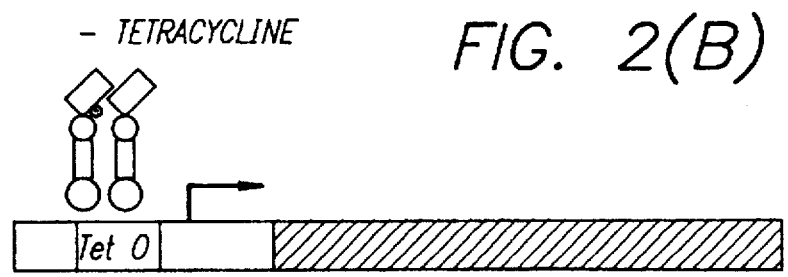
Figure 2C:
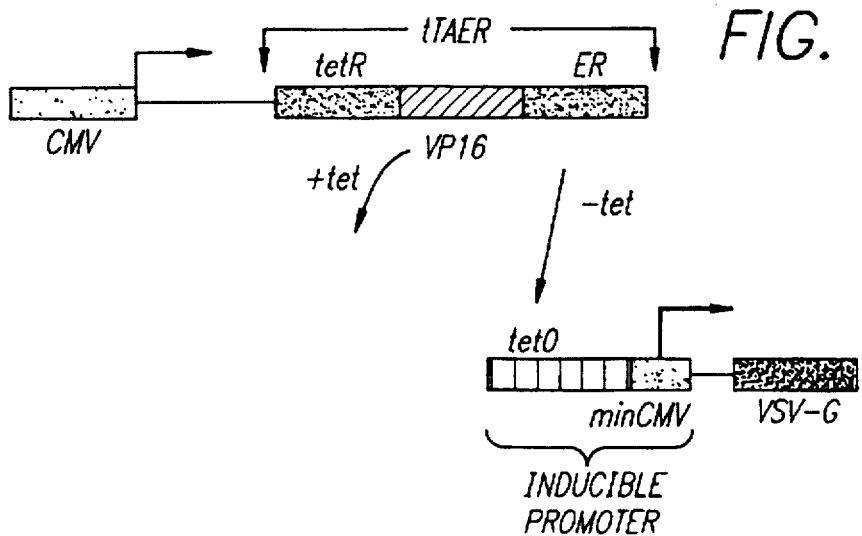

FIGS. 2A, 2B and 2C show schematic illustrations of the basic components of the inducible expression system of the invention. The inducible expression system is composed of at least two major components: 1) a multi-chimeric transactivator; and 2) an inducible promoter, where transcription from the inducible promoter is facilitated by the multi-chimeric transactivator (FIG. 2C). The multi-chimetic transactivator is a fusion protein minimally composed of: 1) a first ligand-binding domain that, when bound to its ligand, negatively affects transcriptional activation by the multi-chimeric transactivator (referred to herein as the binding domain that negatively affects transcription or NAT domain); 2) a transcriptional activation domain (TAD), generally derived from a eukaryotic transcriptional activator; and 3) a second ligand-binding domain without being held to theory, the SLB domain protects the eukaryotic cell in which the multi-chimeric transactivator is expressed from any cytotoxic effects of the transactivator. The domains of the multi-chimeric transactivator are preferably ordered, from N-terminus to C-terminus NAT-TAD-SLB, although the domains may be differently ordered (e.g., from N-terminus to C-terminus, SLB-TAD-NAT).

In a preferred embodiment of the invention, the NAT domain is the repressor of Escherichia coli, (E. coli) tetracycline-resistance operon (tetR), the TAD domain is the activation domain (carboxyl terminal domain) of virion protein 16 (VP16) of herpes simplex virus (HSV) (Triezenberg et al. 1988 Genes Dev. 2:718–729), and the SLB domain is the ligand-binding portion of a steroid receptor, preferably a ligand binding portion of an estrogen receptor (ER), a glucocorticoid receptor (GR), a mineralo-corticoid receptor (MR), an androgen receptor (AR), or a progesterone receptor (PR), more preferably an estrogen receptor. The relative positions of tetR, VP16, ER, and the tetO inducible promoter in the preferred embodiment of the inducible expression system are shown in FIG. 2C.

In general, and as exemplified in FIGS. 2A and 2B, transcription from the inducible promoter is activated when the tetR domain is not bound to tetracycline (a NAT ligand) (FIG. 2B). If ligand is bound to the NAT domain, the multi-chimeric transactivator does not significantly facilitate transcription from the inducible promoter (FIG. 2A).

In one embodiment, the inducible expression system of the invention is composed of: 1) a multi-chimeric transactivator, tTAER, which is a fusion protein composed of (preferably from N-terminus to C-terminus) the *E. coli* tetR polypeptide, the transcriptional activation domain of HSV VP16, and the ligand-binding domain of estrogen receptor (ER); and 2) a minimal promoter derived from the immediate early gene of CMV operably linked to seven tandem copies of tetO, which in turn can be operably linked to a nucleotide sequence of interest.

Transcriptional activation of the tetO inducible promoter by tTAER is inhibited in the presence of tetracycline, which binds to the tetR portion of tTAER. This embodiment is described below in more detail. When the NAT domain of the multi-chimeric transactivator is not bound to a NAT ligand, transcription from the inducible promoter is increased from about 10-fold to about 50-fold, preferably from about 40-fold to 90-fold, more preferably from about 40-fold to 100-fold, and may be 200-fold or more relative to transcription in the presence of NAT ligand. Transcription from the inducible promoter is about 2-fold to about 4-fold, preferably from about 3-fold to 10-fold, greater when the transactivator is not bound by NAT ligand than when the transactivator is bound by NAT ligand.

Preferably, the multi-chimeric transactivator can be expressed at high levels in a eukaryotic cell without significantly adversely affecting general cellular transcription in the host cell, i.e., without significantly eliciting the "squelching" effect associated with high level expression of other transactivator proteins (e.g., tTA of the tetracycline-inducible system of Gossen and Bujard, supra). By "high levels" is meant an amount of multi-chimeric transactivator expression that is sufficient to facilitate transactivation of the inducible promoter, but that is not detrimental to the cell (e.g., is not toxic to the cell). "High levels" can be a level of expression that allows detection of the transactivator by Western blot of about $10^6$ cells or fewer. The multi-chimeric transactivator can preferably be expressed in a wide variety of cell types, including mammalian and non-mammalian cells such as, but not limited to, human, monkey, mouse, hamster, cow, insect, fish, and frog cells.

The multi-chimeric transactivator can be expressed either in vivo or in vitro, and expression of the transactivator can be controlled through selection of the promoter to which the nucleotide sequence encoding the transactivator is operably linked. For example, the promoter can be a constitutive promoter or an inducible promoter. Examples of such promoters include the human cytomegalovirus promoter IE (Boshart et al., 1985 *Cell* 41:521–530), ubiquitously expressing promoters such as HSV-Tk (McKnight et al., 1984 *Cell* 37:253–262) and β-actin promoters (e.g. the human β-actin promoter as described by Ng et al., *Mol. Cell Biol.* 1985 5:2720–2732).

The promoter of the multi-chimeric transactivator can be a cell type-specific or tissue-specific promoter that preferentially facilitates transcription of the transactivator in a desired cell of tissue type. Exemplary cell type-specific and/or tissue-specific promoters include promoters such as albumin (liver specific; Pinkert et al., 1987 *Genes Dev.* 1:268–277), lymphoid specific promoters (Calame et al., 1988 *Adv. Immunol.* 43:235–275); in particular promoters of T-cell receptors (Winoto et al., 1989 *EMBO J.* 8:729–733) and immunoglobulins; Banerji et al., 1983 *Cell* 33729–740; Queen and Baltimore, ibid. 741–748), neuron-specific promoters (e.g. the neurofilament promoter; Byrne et al., 1989 *Proc. Natl. Acad. Sci. USA* 86:5473–5477), pancreas-specific promoters (Edlunch et al., 1985 *Science* 230:912–916) or mammary gland-specific promoters (milk whey promoter, U.S. Pat. No. 4,873,316 and European Application Publication No. 264, 166). Promoters for expression of the multi-chimeric transactivator can also be developmentally-regulated promoters such as the murine homeobox promoters (Kessel et al., 1990 *Science* 249:374–379) or the α-fetoprotein promoter (Campes et al., 1989 *Genes Dev.* 3:537–546). The promoter can be used in combination with control regions allowing integration site independent expression of the transactivator (Grosveld et al., 1987 *Cell* 51:975–985). Preferably, the promoter is constitutive in the respective cell types. Preferably the promoter is a CMV promoter, more preferably a CMV immediate early gene promoter.

Ligand-binding Domain for Inhibition of Transcription by the Multi-Chimeric Transactivator The ligand-binding domain that negatively affects transcription from the inducible promoter (NAT domain of the transactivator) can be derived from any polypeptide that inhibits transcription from a promoter when bound to a specific ligand. Preferably, when bound by its specific ligand, the NAT domain inhibits transcription by preventing binding of the multi-chimeric transactivator to a specific nucleotide sequence within a promoter; more preferably, the specific sequence to which the multi-chimeric transactivator binds to facilitate transcription (when the NAT domain is not bound to its ligand) is a sequence that can be readily incorporated into a desired promoter to facilitate transcriptional regulation of the promoter by multi-chimeric transactivator binding.

The NAT domain can be, for example, a repressor protein that binds a specific DNA sequence in a NAT ligand-dependent manner. Thus, when the NAT ligand is not present, the NAT domain binds the specific nucleotide sequence in the inducible promoter, thus allowing the transcriptional activation domain (TAD) of the multi-chimeric transactivator to facilitate transcription from the inducible promoter. Preferably, binding of NAT domain to the specific nucleotide sequence is relatively tight, e.g., having a binding constant ($k_a$) of at least $10^5$ M$^{-1}$, preferably at least about $10^6$ M$^{-1}$, more preferably at least about $10^8$ M$^{-1}$ to $10^9$ M$^{-1}$, and can be $10^9$ M$^{-1}$ or greater. When the NAT ligand is present, the NAT ligand binds the NAT domain, thereby preventing the NAT domain from binding the specific nucleotide sequence in the inducible promoter, thus inhibiting multi-chimeric transactivation-mediated transcriptional activation. Exemplary NAT domains include, but are not limited to, the repressor (tetR) of the prokaryotic tetracycline-resistance operon, the lac repressor of other prokaryotic lactose operon, GAL4 of the galactose operon (Conner et al., 1993 *Virol.* 195:569, the mammalian jun and creb transactivators (Yin et al. 1995 *J. Virol.* 69:6209–6218) and transactivators found in plants (Wilde et al. 1994 *Plant Mol. Biol.* 24:38).

Preferably, the NAT domain of the multi-chimeric transactivator is a native tetR polypeptide or a functional derivative of tetR, since tetR binds its specific DNA sequence (tetO) with greater affinity than either lacR or GAL4 bind their respective sequences. For example, tetR binds tetracycline much tighter ($k_a \approx 10^9$ M$^{-1}$; Takahashi et al., *J. Mol. Biol.* 187:341–348 (1986) than lacR complexes IPTG ($k_a \approx 10^6$ M$^{-1}$; Barkley & Bourgeios in *The Operon*, Miller & Rezinkoff, eds., Cold Spring Harbor Lab., Cold Spring Harbor, N.Y., 1980, pp. 177–220). Thus, very low, nontoxic concentrations of tetracycline function effectively. By "functional derivative of tetR" is meant a polypeptide derived from tetR that retains both 1) tetracycline or tetracycline analog binding and 2) the ability to inhibit transcription from the inducible promoter by preventing binding of the tetR domain to tetO sequences within the inducible promoter. The nucleotide sequence encoding tetR can be obtained according to Postel et al., 1984 *Nucl. Acids Res.* 2:4849–4863, herein incorporated by reference. Other tetR sequences useful in the invention, and the respective binding sites for these repressors, are described in (Waters et al., 1983 *Nucl. Acids Res.* 11:6089–6105; Postle et al., supra; Unger et al., 1984 *Gene* 31:103–108; Unger et al., 1984 *Nucl. Acids Res.* 127693–7703; Tovar et al., 1988 *Mol. Gen. Genet.* 215:76–80); for comparison and overview see Hillen and Wissmann in *Protein-Nucleic Acid Interaction*, Topics in Molecular and Structural Biology, Saenger and Heinemann (eds.), Macmillan, London, Vol. 10, pp. 143–162 (1989)).

The ligand that binds the ligand-binding domain of the transactivator NAT domain can be the natural ligland that binds the NAT domain or an analog of the natural ligand. Preferably, the natural ligand and/or natural ligand. analog is substantially non-toxic to eukaryotic cells at concentrations required for NAT domain-mediated regulation of the inducible promoter, and can be administered to animals and/or humans at these concentrations with few or no serious side effects.

For example, where the NAT domain is tetR, the natural ligand is tetracycline. Tetracycline analogs can be any one of a number of compounds that are closely related to tetracycline and which bind to the tet repressor with a $K_a$ of at least about $10^6$ $M^{-1}$. Preferably, the tetracycline analogs binds with an affinity of about $10^9$ $M^{-1}$ or greater, e.g., binds with an affinity of about $10^{11}$ $M^{-1}$. Examples of such tetracycline analogs include, but re not limited to those disclosed by Hlavka and Boother, "The Tetracyclines," IN: *Handbook of Experimental Pharmacology* 78, R. K. Blackwood et al. (eds.), Springer-Verlag, Berlin-New York, 1985; Mitschef, "The Chemistry of the Tetracycline Antibiotics," *Medicinal Research* 9, Dekker, New York, 1978; Noyee Development Corporation, "Tetracycline Manufacturing Processes," *Chemical Process Reviews*, Park Ridge, N.J., 2 volumes, 1969; Evans, "The Technology of the Tetracyclines," *Biochemical Reference Series* 1, Quadrangle Press, New York, 1968; and Dowling, "Tetracycline," *Antibiotics Monographs* no. 3, Medical Encyclopedia, New York, 1955; each of which are incorporated herein by reference with respect to tetracycline analogs.

Second Ligand-binding Domain of the Multi-Chimeric Transactivator

The second ligand-binding domain (SLB) can be derived from any polypeptide that provides protection of the eukaryotic host cell from any cytotoxic effects associated with multi-chimeric transactivator expression. Such protection can be provided by regulating the function of the transactivator or by otherwise inhibiting transactivator activities associated with cytotoxicity (e.g., "squelching" effects associated with effects in general cellular transcription) promotes transcription from a promoter when bound to a specific ligand. However, when the transactivator is bound to ligand at its NAT domain (e.g., tetracycline is bound to the tetR domain), the NAT domain inhibits transcriptional activation by the multi-chimeric transactivator, regardless of whether the SLB domain is bound to an SLB ligand.

The SLB domain can be derived from any polypeptide having a ligand-binding domain that, when present in the multi-chimeric transactivator, provides the desired effect (e.g., protects the host cell from transactivator cytotoxicity). Examples of polypeptides having such ligand-binding domains that can be used as an SLB domain in the multi-chimeric transactivator of the invention include, but are not limited to, the ligand-binding domain of thyroid receptors, retinoid receptors, and steroid receptors. Preferably, the PAT domain is a ligand-binding domain of a steroid receptor. The steroid receptor can be a receptor for estrogen (ER; Eilers et al. 1989 *Nature* 340:66–68), glucocorticoid (GR; Picard et al. 1988 *Cell* 54:1073–80), mineralocorticoid (MR; Fankhauser et al. 1994 *Biochem. Biophys. Res. Commun.* 200:195–201), progesterone (PR; Mattioni et al. In: *Methods in Cell Biology*, Chapter 16, 43:335–352) or androgen (AR; Mattioni et al supra). Preferably the steroid receptor is an estrogen receptor (ER). Isolation of the estrogen-binding domain of the estrogen receptor has been described (Kumar et al. 1986 *EMBO J.* 5:2231–2236, herein incorporated by reference with respect to the isolation of the ER ligand-binding domain) and the sequence determined. The ligand that binds the ligand-binding domain of the transactivator's SLB domain can be the natural ligand that binds the SLB domain or an analog of the natural ligand. Preferably, the natural ligand and/or natural ligand analog is substantially non-toxic to eukaryotic cells at concentrations required for SLB domain-mediated effects, and can be administered to animals and/or humans at these concentrations with few or no serious side effects.

For example, where the SLB domain of the multi-chimeric transactivator is derived from a ligand-binding domain of an estrogen receptor (ER), the natural ligand is estrogen. Estrogen analogs that can be used with ER-containing transactivators include 17β-estradiol, 17β-estradiol, 17α-estradiol, and other estrogen and estradiol derivatives that can bind the estrogen-binding domain of the estrogen receptor.

Without being held to theory, the SLB domain can mediate prevention or decrease of the cytotoxic effect of the transactivator by either SLB ligand mediated regulation of transactivator function or some other mechanism that prevents the "squelching" effect of the tetR-VP16 (NAT-TAD) fusion protein portion (referred to as tTA by Gosseu and Bujard, supra) previously described. Where the SLB domain is a ligand-binding domain of a steroid receptor and the SLB domain serves to prevent transactivator cytotoxicity through regulation of transactivator functioning, inactivation of the transcriptional activation function by the multi-chimeric transactivator is mediated by a complex containing heat-shock protein 90 (HSP90) (Picard et al 1988 supra; Yamamoto et al. 1988 *Cold Springs Harber Symp. Quant. Biol.* 53:803–811; Picard 1993 *Trends Cell Biol.* 3:278–280). HSP90, as well as several other proteins, is associated with the unbound steroid-binding domains of all five vertebrate steroid receptors (ER, GR, AR, MR and PR) (Pratt 1990 *Mol. Cell. Endocrinol.* 74:C69–76; Smith et al. 1993 *Mol. Endocrinol.* 7:4–11). Steroid binding results in release of the HSP90 complex, and functional activation of the transactivator to mediate transcriptional activation from the inducible promoter. Thus, where the SLB domain regulates multi-chimeric transactivator function in this manner, transcription from the inducible promoter occurs primarily only in the presence of SLB ligand and the absence of tetracycline. The steroid-reversible protein inactivation function of the steroid-binding domain may work via a mechanism involving steric hindrance by the HSP90 complex. Thus, any SLB domain having a ligand-binding portion that, when unbound by ligand, binds an HSP90-containing complex and sterically hinders transactivation by the multi-chimeric transactivation is suitable for use in the present invention.

Transcriptional Activation Domain

The transcriptional activation domain can be derived from any transcriptional activator. In general, the transcriptional activation domains are polypeptide sequences having a distinct conformational and/or charge characteristics. For example, "acid blob" domains are transcriptionat domains of HSV transcriptional activators that facilitate transcriptional activation through interaction of the domain's highly negatively charged polypeptide sequence with proteins essential for transcriptional activation (see Triezenberg et al. 1988 *Genes Dev.* 2:718–729). Preferably, the transcriptional activation domain of the multi-chimeric transactivator is the negatively charged C-terminal domain of VP16, the transactivator of herpes simplex virus immediate early gene expression, described in Triezenberg et al. 1988 *Genes Dev.* 2:718–729, which is herein incorporated by reference with respect to the transcriptional activation domain of VP16. Preferably, the transcriptional activation domain of the multi-chimeric transactivator is composed of the C-terminal 130 amino acids of VP16.

description and sequence of tetO. Other tetO sequences that can be used in the practice of the invention can be obtained from the following references: Waters et al., 1983, supra; Postle et al., 1984, supra; Unger et al., 1984, supra; Unger et al., 1984, supra; Tovar et al., 1988, supra; for comparison and overview see Hillen and Wissmann 1989, supra, the disclosures of which are fully herein incorporated by reference. One, two, three, four, five, six, seven, eight, nine or ten or more copies of the tet operator sequence can be used. Because multiple copies of the tet operator sequence provide a synergistic effect on the ability to control expression from these tetO-containing promoter, promoters having a greater number of copies of tetO allow an enhanced range of transactivator regulation of transcription from the promoter. Regulation of tetracycline-regulatable promoters containing tetO sequences is discussed in U.S. Pat. No. 5,464,758, and in Gossen and Brujand, 1992 *Proc. Natl. Acad. Sci. USA* 89:5547–5551, each of which are herein incorporated by reference. The sequence of the inducible promoter is provided below.

| SEQUENCE OF INDUCIBLE PROMOTER | | | | | | | |
|---|---|---|---|---|---|---|---|
| 1   | CTCGAGttta | ccactcccta | tcagtgatag | agaaaagtga | aagtcgagtt | taccactccc | 60 |
| 61  | tatcagtgat | agagaaaagt | gaaagtcgag | tttaccactc | cctatcagtg | atagagaaaa | 120 |
| 121 | gtgaaagtcg | agtttaccac | tccctatcag | tgatagagaa | aagtgaaagt | cgagtttacc | 180 |
| 181 | actccctatc | agtgatagag | aaaagtgaaa | gtcgagttta | ccactcccta | tcagtgatag | 240 |
| 241 | agaaaagtga | aagtcgagtt | taccactccc | tatcagtgat | agagaaaagt | gaaagtcgag | 300 |
| 301 | ctcggtaccc | gggtcgagTA | GGCGTGTACG | GTGGGAGGcC | TATATAAGCA | GAGCTCGTTT | 360 |
| 361 | AGTGAACCGT | CAGATCGCCT | GGAGACGCCA | TCCACGCTGT | TTTGACCTCC | ATAGAAGACA | 420 |
| 421 | CCGGGACCGA | TCCAGCCTCC | GCGGCCCCGA | ATTCGAGCTC | GGTACCCGGG | GATCCtctaga | 481 |

(SEQ ID NO:1)

Inducible Promoters

In general, the inducible promoter used in conjunction with the transactivator in the inducible expression system of the invention is any promoter from which transcription can be regulated by the multi-chimeric transactivator in a NAT ligand-dependent manner. For example, when the transactivator is bound to ligand at its NAT domain (e.g., a tetR domain), the transactivator cannot bind to the inducible promoter, and transcription does not occur at a significant level.

The composition of the inducible promoter is correlated with the relevant components of the multi-chimeric transactivator, and can be present as multiple, tandemly repeated copies. For example, where the transactivator NAT domain is a tetR polypeptide, the inducible promoter is preferably a minimal promoter containing at least one tetO sequence, preferably at least 2 or more tandemly repeated tetO sequences, even more preferably at least 5 or more tandemly repeated tetO sequences, most preferably at least 7 tandemly repeated tetO sequences or more. Alternatively, where the NAT domain is derived from lacR, the inducible promoter contains at least one laci sequence. The minimal promoter portion of the inducible promoter can be derived from any desired promoter, and is selected according to tet cell line in which the inducible expression system is to be used. Where the cell is a mammalian cell, a preferred minimal promoter is derived from CMV, preferably from the CMV immediate early gene 1A.

Preferably, the inducible promoter is a minimal promoter operatively linked to at least one tet operator (tetO) sequence. The tetO sequence can be obtained, for example, according to Hillen & Wissmann 1989, supra, each of which are herein incorporated by reference with respect to the Constructs The basic components of the inducible expression system, e.g., the nucleotide sequence encoding the transactivator and the inducible promoter operably linked to a nucleotide sequence of interest, can be contained within a single construct or within two separate constructs. The construct can be derived from any of a variety of constructs know in the art and/or commercially available, and can be capable of replication in prokaryotic cells, eukaryotic cells, or, preferably, both prokaryotic and eukaryotic cells.

In addition to the components described above, the construct can additionally contain nucleotide sequence encoding gene(s) that can serve as selectable markers, e.g., antibiotic resistance genes (e.g., ampicillin, hygromycin, G418), β-galactosidase, or other gene products that can be used for selection of cells containing the construct. The construct can additionally contain other expression-facilitating sequences, such as enhancers, introns, or other sequences that facilitate expression of the transactivator and/or, where appropriate, expression of the nucleotide sequence of interest operably linked to the inducible promoter.

Introduction of the Inducible Expression System into Host Cells

Any eukaryotic cell line that can be stably transformed with the inducible expression system of the invention and the nucleotide sequence(s) expressing the essential retroviral components (e.g., Gag and Pol), and express sufficient levels of the essential retroviral components and inducibly express the desired envelope protein for the production of recombinant retroviral vectors according to the invention can be used to generate a packaging cell line according to the invention. Suitable host cells include cells of both mammalian (e.g., human, simian, canine, feline, equine, and rodent) and non-mammalian origin (e.g., insect, reptile, fish and avian). The packaging cells can be either an in vitro cell culture or present in an organism in vivo.

Preferably, the packaging cells are present in an in vitro culture and can be cultured in a manner that allows for mass production of the recombinant retroviral vectors so as to provide suitable titers useful for production of the retroviral vector preparations for various applications (e.g., for clinical application in gene therapy). Where large-scale production of virus is desirable, the host cell from which the packaging cell is derived is preferably easy to culture, stable in long term culture (e.g., healthy cells can be maintained at relatively high cell densities for several days to several weeks or months, and do not undergo any significant genetic changes that might affect reliable production of consistent retroviral vector titers and/or the homogeneity of the genetic composition of the retroviral particles), and allows easy isolation of virus from the cell culture (e.g., by collection and concentration of cell culture supernatant to provide a crude retroviral particle preparation of an acceptable viral titer).

Preferably, the inducible expression system is introduced into a host cell as a single recombinant nucleotide sequence (e.g., rather than as two separate sequences, one encoding the transactivator and one encoding the gene product of interest under control of the inducible promoter). Introduction of the nucleotide sequence encoding the inducible expression system into host cells can be accomplished either in vitro or in vivo according to methods well known in the art (see, e.g., Sambrook et al., 1987 *Molecular Cloning: A Laboratory Manual*, Cold Spring Harbor Press, Cold Spring Harbor, N.Y. In a preferred embodiment, the inducible expression system is introduced into the host cell by infection with a retroviral vector containing the nucleotide sequence encoding the multi-chimeric transactivator and/or the inducible promoter operably linked to the nucleotide sequence encoding the desired envelope protein, and the nucleotide sequence encoding the inducible expression system is stably integrated into the host cell genome.

Packaging Cell Lines Using the Inducible Expression System

The inducible expression system of the invention is used to generate packaging cells useful in the production of recombinant pseudotyped retroviral vectors, which are suitable for use in the introduction of a DNA sequence of interest into a target cell. Pseudotyped retroviral particles are retroviral particles having an envelope protein that is derived from a virus other than the virus from which the viral RNA genome is derived. The envelope protein can be from a retrovirus of a species different from the retrovirus from which the RNA genome is derived or from a non-retroviral virus (e.g., vesicular stomatitis virus (VSV)). Normally, the pseudotyped retroviral vectors, are defective, i.e., the retroviral vector is derived from a naturally-occurring virus that has been genetically altered to render the virus replication-defective. Once the virus delivers its genetic material into a target cell, the virus introduces the recombinant nucleotide sequence into cell, preferably as a stably chromosomally integrated sequence, but does not generate additional infectious virus upon expression of the introduced retroviral sequence. Alternatively, the retroviral vector containing the nucleotide sequence of interest is attenuated, i.e. does not cause significant pathology or morbidity in the infected host (i.e., the virus is nonpathogenic or causes only minor disease symptoms).

Pseudotyped retroviral particles can be produced by introducing a defective, recombinant retrovital genome into a packaging cell (e.g., by infection with a defective retroviral particle, or by other means for introducing DNA into a target cell (e.g., conventional transformation techniques)). The defective retrovital genome minimally contains the long terminal repeats, the exogenous nucleotide sequence of interest to be transferred, and a packageing sequence ($\phi$). In general, the packaging cell provides the missing retroviral components essential for retrovital replication, integration, and encapsidation, and also expresses a nucleotide sequence encoding the desired envelope protein. However, the packaging cell does not have all of the components essential for the production of retroviral particles. The nucleotide sequence(s) encoding the missing viral component(s) in the packaging cell can be either stably integrated into the packaging cell genome, and/or can be provided by a co-infecting helper virus.

The nucleotide sequences encoding the retroviral components and the retroviral RNA genome can be derived from any desired retrovirus (e.g., murine, simian, arian, or human retroviruses). Most defective retroviruses developed for gene therapy applications are murine retroviruses (e.g., murine leukemia virus (MuLV), Moloney murine leukemia virus (MoMLV)), (see, e.g., Miller et al. 1992 *Nature* 357:455–460; and Mulligan 1993 *Science* 260:926–932). In general, the retroviral components can be derived from any retrovirus that can form pseudotyped retroviral particles with the desired envelope protein, e.g., VSV G. Where VSV G is the desired envelope protein, the retroviral components can be derived from MuLV, MoMLV, avian leukosis virus (ALV), human immunodeficiency virus (HIV), or any other retrovirus that can form pseudotyped virus with VSV G as the only envelope protein or with VSV G and a relatively small amount of retroviral envelope protein.

In one example of a pseudotyped retrovirus produced according to the present invention, the free virion form of pseudotyped defective murine retrovirus contains the structural and enzymatic proteins of the retrovirus (including reverse transcriptase), two RNA copies of the retroviral genome, and portions of the cell's plasma membrane in which is embedded the desired viral envelope glycoprotein (e.g., VSV G). The genome is organized into four main regions: the long terminal repeat (LTR), the gag gene, the pol gene, and the env gene. The three genes gag, pol, and env, which are located between the terminal LTRs, encode internal viral structural proteins and reverse transcriptase, respectively, and the env gene encodes the envelope glycoprotein that confers infectivity and host range specificity to the virus. Preferably, the retroviral genome is defective in one or all three of these genes. In addition, the retroviral genome can contain a nucleotide sequence of interest to be ultimately transferred to a target cell. When the defective, recombinant retroviral genome is integrated into the host cell in its proviral form, the LTR is positioned at both ends of the proviral genome, and is a composite of the 5' and 3' ends of the RNA genome. The LTR contains cis-acting elements necessary for the initiation and termination of transcription.

An exemplary packaging cell of the invention contains genes encoding Gag and Pol, as well as the desired envelope protein, but does not contain the packaging signal "$\phi$" or the LTRs described above. Thus, a packaging cell can only form empty virion particles; once a retroviral RNA genome (which contains the nucleotide sequence of interest) is introduced into the packaging cell, the packaging cell can produce pseudotyped, defective retrovital particles. Packaging cells thus provide the missing retroviral components (i.e., the components for which the retroviral genome is defective) essential for viral replication in trans. Methods for production of replication-deficient retroviral genomes containing a nucleotide sequence of interest, as well as methods for generating a cell line expressing the gag and pol genes, are well known in the art and are described in, for example, U.S. Pat. No. 4,861,719; PCT published application no. WO 92/05266, published Apr. 2, 1992; and PCT published application no. WO 92/14829, published Sep. 2, 1992, each of which are incorporated herein by reference with respect to production of replication-deficient retroviral genomes and packaging cell lines expressing retroviral gag and pol genes. Retroviral packaging cell lines can be derived from any mammalian or non-mammalian cell that can express the retroviral Gag and Pol proteins, and can express the desired envelope protein (e.g., can tolerate expression of VSV G for several hours to several days, preferably for at least one week to two weeks or more). Preferably, the cell line from which the packaging cell line is derived is a HeLa (ATCC CCL 2), D17 (ATCC CCL 183), MDCK (ATCC CCL 34), BHK (ATCC CCL-10), or Cf2Th (ATCC CRL 1430) cell, most preferably a Cf2Th cell, each of which are publicly available from the ATCC.

Pseudotyped retroviral particles are produced according to the invention by introducing a defective, recombinant retroviral genome containing a nucleotide sequence of interest into a packaging cell line that, contains nucleotide sequences encoding for 1) functional retroviral proteins for which the introduced RNA genome is defective (e.g., gag and pol), and 2) an inducible expression system of the invention that facilitates expression of a desired envelope protein. The defective, recombinant RNA genome can be introduced into the packaging cell line by any means, including infection with a defective viral particle or other conventional means of transformation. Preferably, the packaging cell expresses a retroviral Gag protein, a retroviral Pol protein, and a desired envelope protein that is inducibly expressed using the system of the invention. The inducible expression system contained within the packaging cell line is composed of 1) a nucleotide sequence encoding a multi-chimeric transactivator, and 2) a nucleotide sequence composed of an inducible promoter operably linked to a nucleotide sequence encoding the desired envelope protein. The inducible expression system can be introduced as a single construct or as multiple constructs as described above.

Preferably, the multi-chimeric transactivator is a fusion protein composed of a tetR domain, a transcriptional activation domain (preferably a transcriptional activation domain of VP16), and a ligand-binding domain of a steroid receptor (preferably a ligand binding domain of an estrogen receptor). The inducible promoter is preferably a minimal promoter derived from a CMV early gene promoter which is operably linked to at least one tetO sequence, preferably at least 2 or more tandemly repeated tetO sequences, even more preferably at least 5 or more tandemly repeated tetO sequences, most preferably at least 7 tandemly repeated tetO sequences or more.

The nucleotide sequence encoding the desired envelope protein for production of retroviral particles is preferably a nucleotide sequence encoding a viral envelope protein derived from a virus other than the virus from which the Gag, Pol, and/or RNA genome are derived. Preferably, the viral envelope protein is derived from a retrovirus (e.g., a xenotropic retrovirus, a polytropic virus, or an amphotropic virus, preferably an amphotropic virus) or a non-retroviral virus, e.g., a rhabdovirus. In a preferred embodiment, the nucleotide sequence encoding the desired envelope protein encodes a rhabdovirus envelope G protein, such as the envelope protein of vesicular stomatitis virus (VSV), or a functional derivative thereof.

The nucleotide sequence encoding VSV G is described in Rose et al. 1982 *Cell* 30:753–762, herein incorporated by reference with respect to disclosure of the VSV G nucleotide and amino acid sequences. Where the desired envelope protein is VSV G, VSV G can be present as the only envelope protein in the pseudotyped retroviral virion, or can be present in combination with other envelope proteins (e.g., the retroviral envelope protein normally associated with the retrovirus from which the retroviral components of other pseudotyped virion are derived). Preferably, VSV G is present in the viral envelope such that VSV G represents about 50% of the envelope proteins present in the viral envelope, more preferably about 75%, even more preferably about 90% to about 95%, still more preferably greater than 95%, most preferably about 100% or such that VSV G is substantially the only envelope protein in the viral envelope. VSV G can be a native (i.e., naturally-occurring) VSV G, or a functional derivative thereof.

Functional derivatives of VSV G include, but are not limited to, VSV G-derived polypeptides having amino acid substitutions, deletions, additions, and/or chemical modifications relative to native VSV G. Functional VSV G derivatives thus include, but are not limited to, VSV G-derived polypeptides having a function different from or in addition to that normally associated with native VSV G. For example, VSV G can be fused to a polypeptide derived from an antibody having binding affinity for a tissue-specific or cell-specific antigen. Pseudotyped viral particles having such a VSV G-single chain antibody fusion protein present in the viral envelope can preferentially infect cells expressing on their surface the antigen to which the antibody chain binds. Other VSV G functional derivatives can likewise alter the host cell range of the pseudotyped viral particle and/or provide other desired characteristics. In general, any VSV G functional derivative that can form pseudotyped retroviral virions according to the invention can be used.

When the envelope-expressing packaging cell is exposed to tetracycline (or an analog thereof), substantially no or very little VSV G is expressed from the inducible promoter. In the absence of tetracycline, expression of the envelope protein is increased from about 10-fold to about 50-fold, preferably from about 40-fold to 90-fold, more preferably from about 40-fold to 100-fold, and may be 200-fold or more relative to transcription in the presence of tetracycline. In addition, expression of the multi-chimeric transactivator can be regulated by operably linking the nucleotide sequence encoding the multi-chimeric transactivator to a regulatable promoter. Thus the packaging cell of the invention can provide two or more levels of regulation of expression of the desired envelope protein: 1) negative regulation of expression of the envelope protein by the addition of tetracycline; 2) positive regulation by removing tetracycline; and, optionally, 3) regulated expression of the nucleotide sequence encoding the multi-chimeric transactivator.

The packaging cell line of the invention capable of inducible expression of a desired envelope protein can be used to produce pseudotyped retroviral vectors at pre-centrifugation viral titers of at least more than $10^4$/ml, preferably more than $10^5$/ml, even more preferably more than $10^6$/ml. Preferred packaging cell lines of the invention produce viral titers of at least $10^5$ infectious particles per ml, preferably at least $5 \times 10^5$ per ml, more preferably at least $10^6$ per ml, and can produce viral titers of $1 \times 10^7$ per ml or more. Preferred packaging cell lines can produce viral titers on the order of at least about 1 viral particle/cell, preferably about 10 viral particles per cell, more preferably about 100 viral particles per cell or more. Preferred packaging cell lines can also be characterized by a viral titer produced over a unit of time. For example, preferred packaging cells of the invention produce about $10^4$ infectious particles per ml per hour, preferably about $10^5$ particles per ml per hour, and can produce up to about $10^6$ particles per ml per hr or more.

The packaging cells can be maintained under conditions that allow for production of infectious pseudotyped virions (e.g., in the absence of tetracycline) for at least 4 days, preferably at least 7 days, even more preferably at least 12 days, and can be maintained for 16 days or longer. For example, Cf2Th cells can be maintained at least 7 days after induction with high virus productivity (e.g., from about $10^4$ to about $10^6$ cfu/ml or greater). Preferably, the packaging cells provide a higher titer in a shorter period of viral production time (i.e., as opposed to a lower viral titer over a longer period of viral production.

Preferably, the packing cells of the invention respond within a short time after induction, i.e., the packaging cells respond quickly to produce pseudotyped virus when NAT ligand (e.g., tetracycline) is removed from the media. Preferably, the packaging cells produce detectable viral titers within 48 hours after induction, more preferably within 12 hours to 24 hours after induction. Preferably, the packaging cells of the invention produce viral titers of at least $10^3$ cfu/ml, more preferably at least $10^4$ cfu/ml, still more preferably at least $10^5$ cfu/ml, most preferably $10^6$ cfu/ml or more within 5 days after induction, preferably within 4 days after induction, more preferably within 3 days after induction, still more preferably within 2 days after induction, and may produce such viral titers within 48 hours to 36 hours or less after induction.

In general, the pseudotyped virus packaging cell lines of the invention can produce $10^4$ to $10^6$ infectious viral particles per ml, provide virus production within a short time (e.g., within 24 hours to 48 hours) after removal of NAT ligand (e.g., tetracycline) and can produce infectious virus for about 5 days to about 16 days or more.

The packaging cells of the invention are preferably derived from cells that are easy to maintain in culture, can be grown to high densities, can be efficiently transfected using conventional techniques, and can tolerate levels of the multi-chimeric transactivation and desired envelope protein necessary to allow inducible expression of viral envelope and production of pseudotyped retroviral vectors. Repression of envelope protein production is preferably very tight (e.g., even a small amount of NAT ligand (e.g., tetracycline), results in repression of viral envelope expression, and response to induction of expression is rapid (e.g., preferably within 12 hours to 36 hours after removal of NAT ligand). For example, Cf2Th cells grow like regular fibroblasts, are easy to culture, and exhibit a high DNA transfection efficiency (e.g., by the conventional calcium-phosphate co-precipitation method), making genetic manipulation of this cell line very easy.

In one embodiment, the packaging cells are present within a transgenic animal for in vivo production of pseudotyped retroviral particles that can be harvested from the animals (e.g., by collecting and isolating pseudotyped virions from the animal's blood or any other body fluid). The nucleotide sequence(s) encoding the retroviral Gag and Pol proteins and the nucleotide sequence(s) encoding the inducible expression system can be used to generate transgenic animals according to methods well known in the art as described above. The animals can then be infected with infectious, replication defective retroviral virions containing the nucleotide sequence of interest, which can then infect the "in vivo" packaging cells present in the transgenic animal to produce high titers of pseudotyped retroviral vector particles. Expression of the envelope protein encoded by the inducible expression system can be regulated by administration of tetracycline to the transgenic animal as described above.

The pseudotyped retroviral vector particles generated using the packaging cells of the invention can be used to facilitate delivery of a nucleotide sequence of interest to a host cell either in vitro or in vivo. For example, the pseudotyped retroviral vector particles can be used in gene therapy applications to deliver therapeutic gene product-encoding sequence to a subject, e.g., a mammalian subject, preferably a human subject. The pseudotyped retroviral vector particles can also be used to develop various disease or development animal or in vitro models. Methods for administration of retroviral particles to a subject to accomplish in vivo transformation are well known in the art (see, e.g., Mulligan 1993 Science 260:926; Anderson 1992 Science 256:808; Miller 1992 Nature 357:455; Crystal 1995 Science 270:404). Methods for transformation in vitro using retroviral particles are also well known in the art.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1
Constructs for use in the inducible expression system

Figure 3:
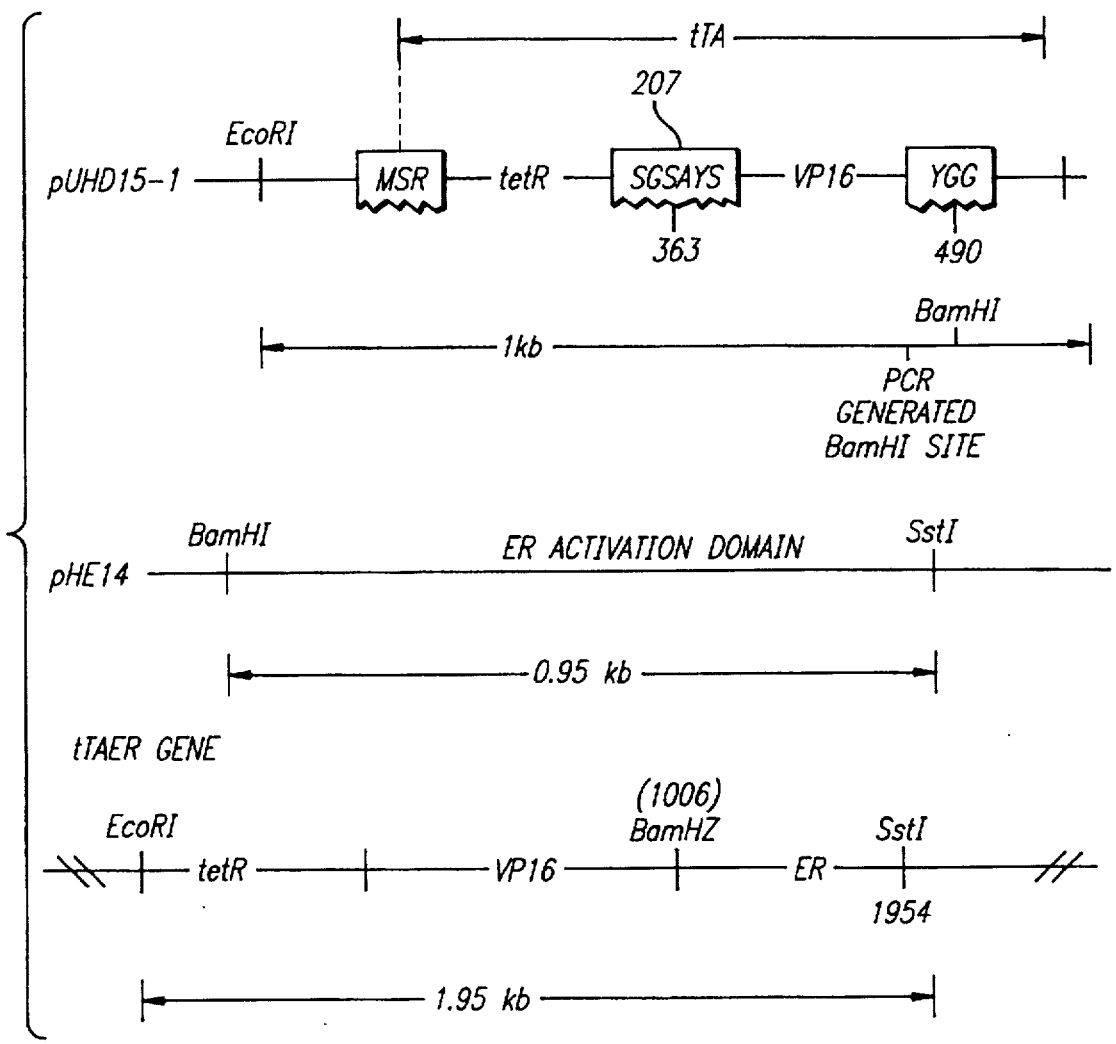
FIG. 3 is a schematic illustration of the production of tTAER, an exemplary multi-chimeric transactivator of the invention.
Figures 1, 15:
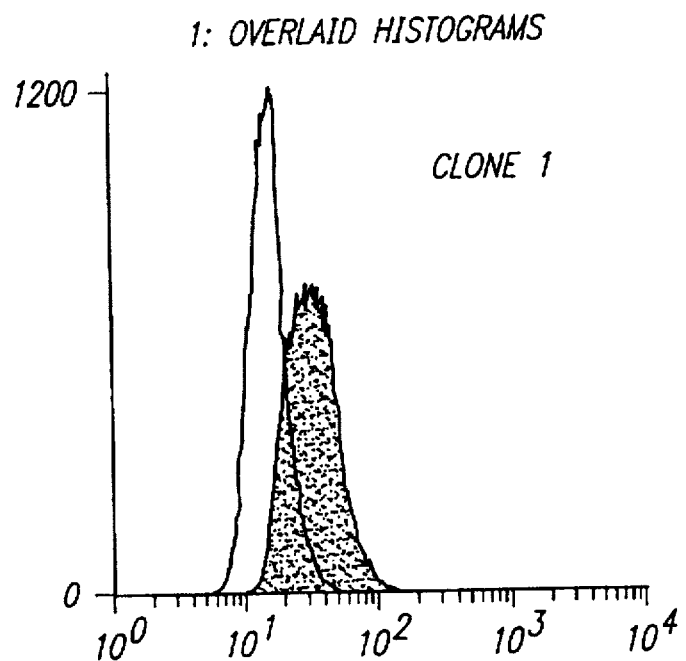
FIG. 15 is a set of 6 graphs showing flow cytometric analysis of inducible cell surface VSV-G expression in TEPN-G virus-infected HT1080 cells. Horizontal and vertical axes measure fluorescence intensity and cell number, respectively.
Figures 2, 15:
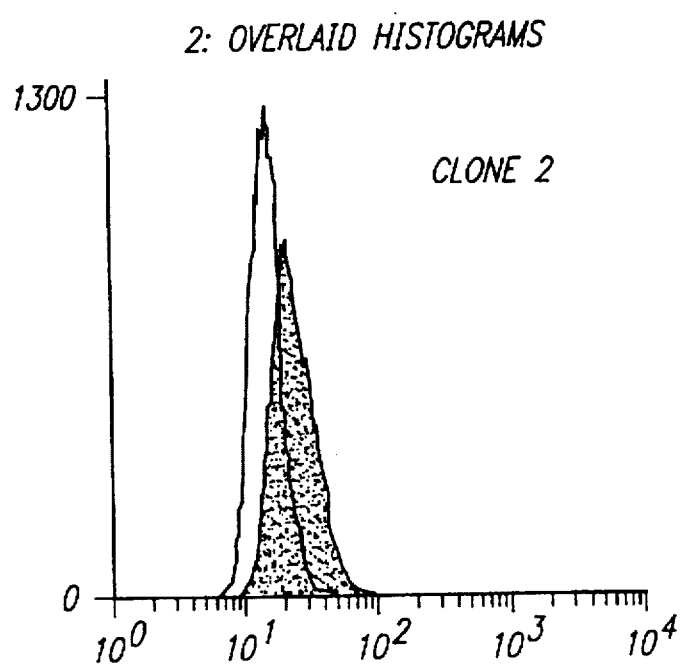
Figures 3, 15:
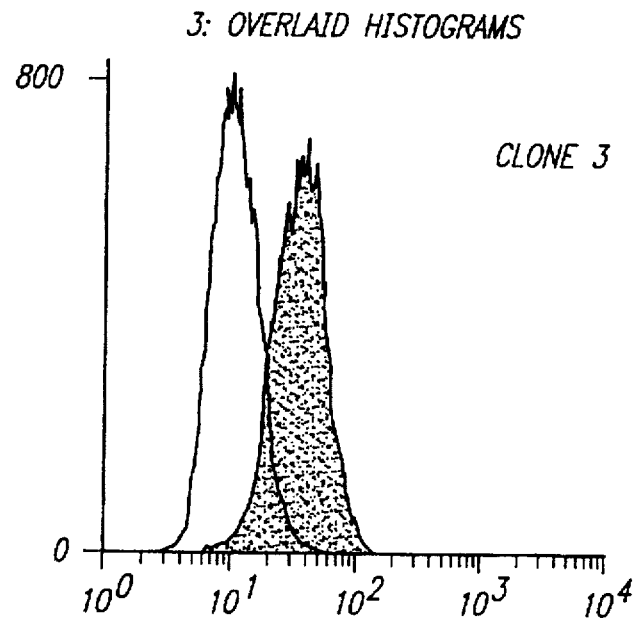
Figures 4, 15:
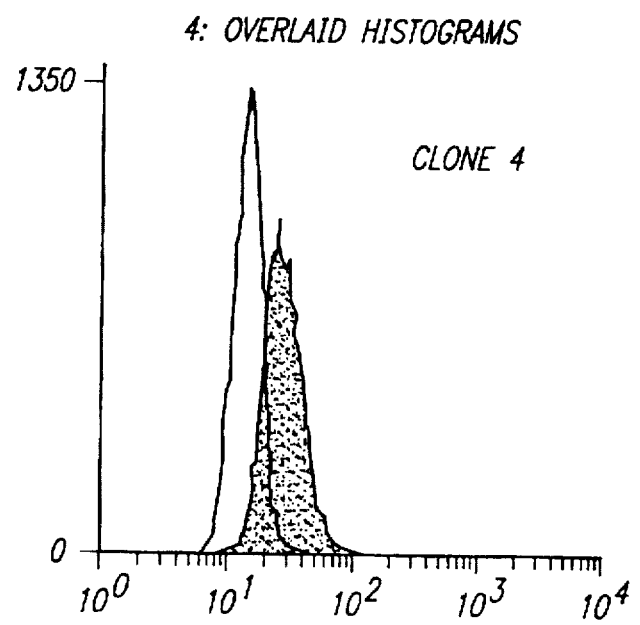
Figures 5, 15:
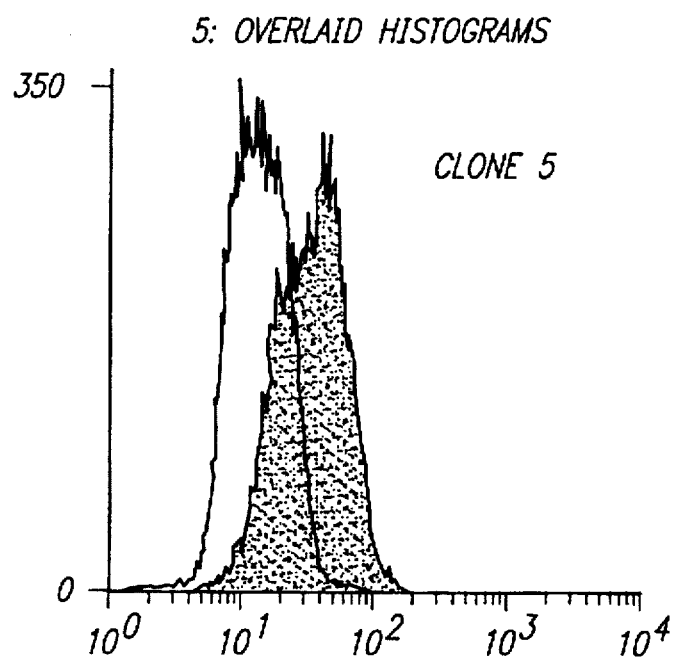
Figures 6, 15:
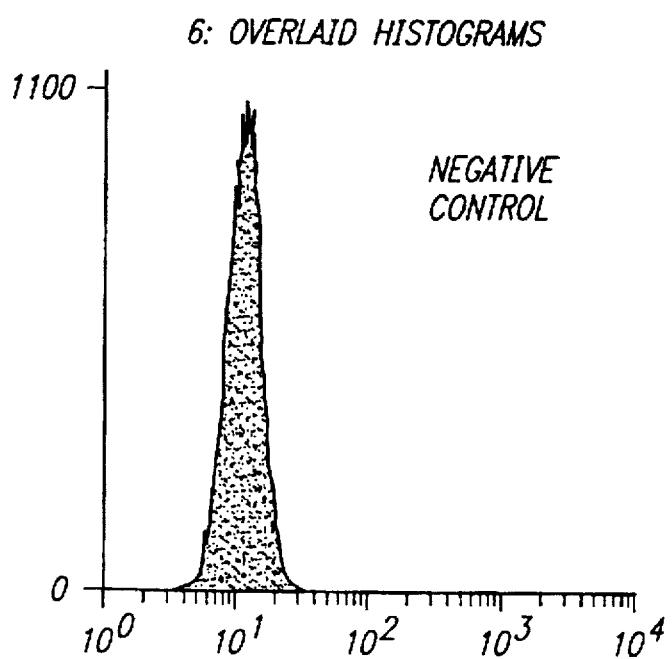

The nucleotide sequence encoding the multi-chimeric transactivator tTAER was generated by isolating a 1-kilobase pair (kb) EcoRI-BamHI DNA fragment containing the tTA gene from the construct pUHD15-1 (Gossen et al., 1992 supra) (FIG. 3). The 1 kb EcoRI-BamHI fragment was ligated to a 0.95-kb BamHI-SstI DNA fragment containing the estrogen receptor (ER) ligand-binding domain from pHE14 (Kumar et al., 1986 EMBO J. 5:2231–2236) (FIG. 3). The resulting construct encodes tTAER, which is composed of (from N-terminus to C-terminus) tetR, the activation domain of VP16, and the ER (FIG. 3). The nucleotide and amino acid sequences of tTAER are shown in FIGS. 4A–4C.

Several constructs were prepared to test the expression and function of tTAER, and to produce stable cell lines expressing tTAER. The construct pCMV-tTAER (FIG. 5) was generated by inserting the 1.95-kb EcoRI fragment containing the complete tTAER gene into the unique BamHI site in pCMV-Bam (Yee et al., 1994, supra); expression of tTAER from the pCMV-tTAER construct is under the control of the CMV immediate early gene 1A promoter. The construct phyg-CMV-tTAER (FIG. 5), used in the production of stable cell lines, was prepared by isolating a 2.0-kb BamHI-HindIII DNA fragment containing the gene encoding hygromycin B phosphotransferase (hygR; Gritz et al., 1983 Gene 25:179–188) under the control of the HSV thymidine kinase (TK) promoter from pTK-hyg. This hygR-encoding fragment was then inserted at the unique NotI site immediately upstream of the CMV immediate early gene promoter in pCMV-tTAER. The pTetO-CAT construct (FIG. 6) was generated by inserting a 1.5-kb BamHI-HpaI DNA fragment containing the gene encoding the bacterial chloramphenicol acetyltransferase (CAT) (isolated from pTKCAT (Yee, J. K., 1989 Science 246:658–661) into the unique BamHI site of pUHG10-3 (Furth et al., 1994 Proc. Natl. Acad. Sci. USA 91:9302–9306). The pTEPN construct (FIG. 6) was generated isolating the 2-kb EcoRI DNA fragment containing the tTAER gene from pCMV-tTAER and inserting this fragment into the unique BamHI site of pLPONL6 (Yee et al., 1994 Proc. Natl. Acad. Sci. USA. 91:9564–9568).

Several constructs having promoters inducible by tTAER were prepared to test tTAER expression and function. The pTetO-G-1 construct (FIG. 5) was prepared by isolating a 1.6-kb BamHI DNA fragment containing the VSV-G gene from pCMV-G (Yee et al., 1994, supra) and inserting the VSV-G-encoding fragment at the unique BamHI site in pUHG10-3 (Gossen et al., 1992, supra). The pTetO-G-2 construct (FIG. 5) was prepared by isolating a 2.3-kb BamHI DNA fragment containing the gene encoding puromycin-N-acetyltransferase (purR; Lacalle et al., 1989 Gene 79:379–384) under the control of the HSV TK promoter from pTK-pur. The purR-encoding fragment was then inserted at the unique BglII site downstream from the VSV-G gene in pTetO-G-1. The pLZRNL construct (FIG. 5; Xu et al., Virology 171:331–341, 1989) which was used to produce LZRNL virus, containing the E. coli lacZ gene operably linked to a 5'LTR and contains the neomycin phosphotransferase (neo) gene operably linked to an RSV LTR promoter.

Figure 5:
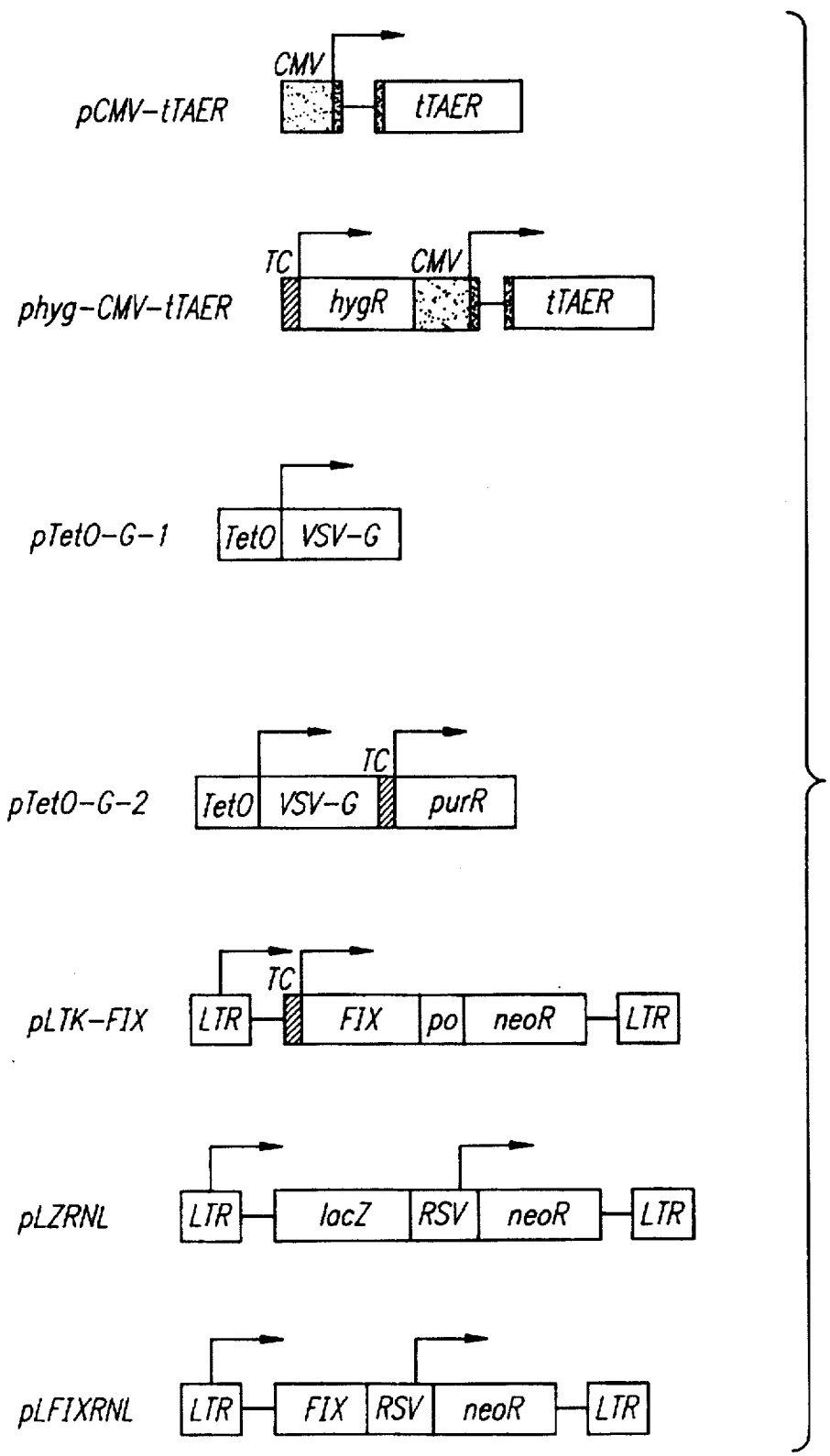
FIG. 5 is a schematic illustration of the constructs pCMV-tTAER, phyg-CMV-tTAER, pTetO-G-1, pTetO-G-2, and pLTK-FIX. The stippled boxes represent the promoter of the CMV immediate early gene. The hatched boxes represent the HSV TK promoter. tTAER, the gene encoding tTAER; hygR, the gene encoding hygromycin B phosphotransferase; purR, the gene encoding puromycin-N-acetyltransferase; neoR, the neomycin phosphotransferase gene; tetO, the minimum CMV immediate early gene promoter linked to seven tandem copies of the tetR binding site; VSV-G, the gene encoding VSV-G; LTR, the long terminal repeat of MoMLV; FIX, the canine factor IX cDNA; po, the internal ribosome entry site of poliovirus. Arrows indicate the approximate locations of the transcription initiation sites and the direction of transcription. The figure is not drawn to scale.
Figure 6:
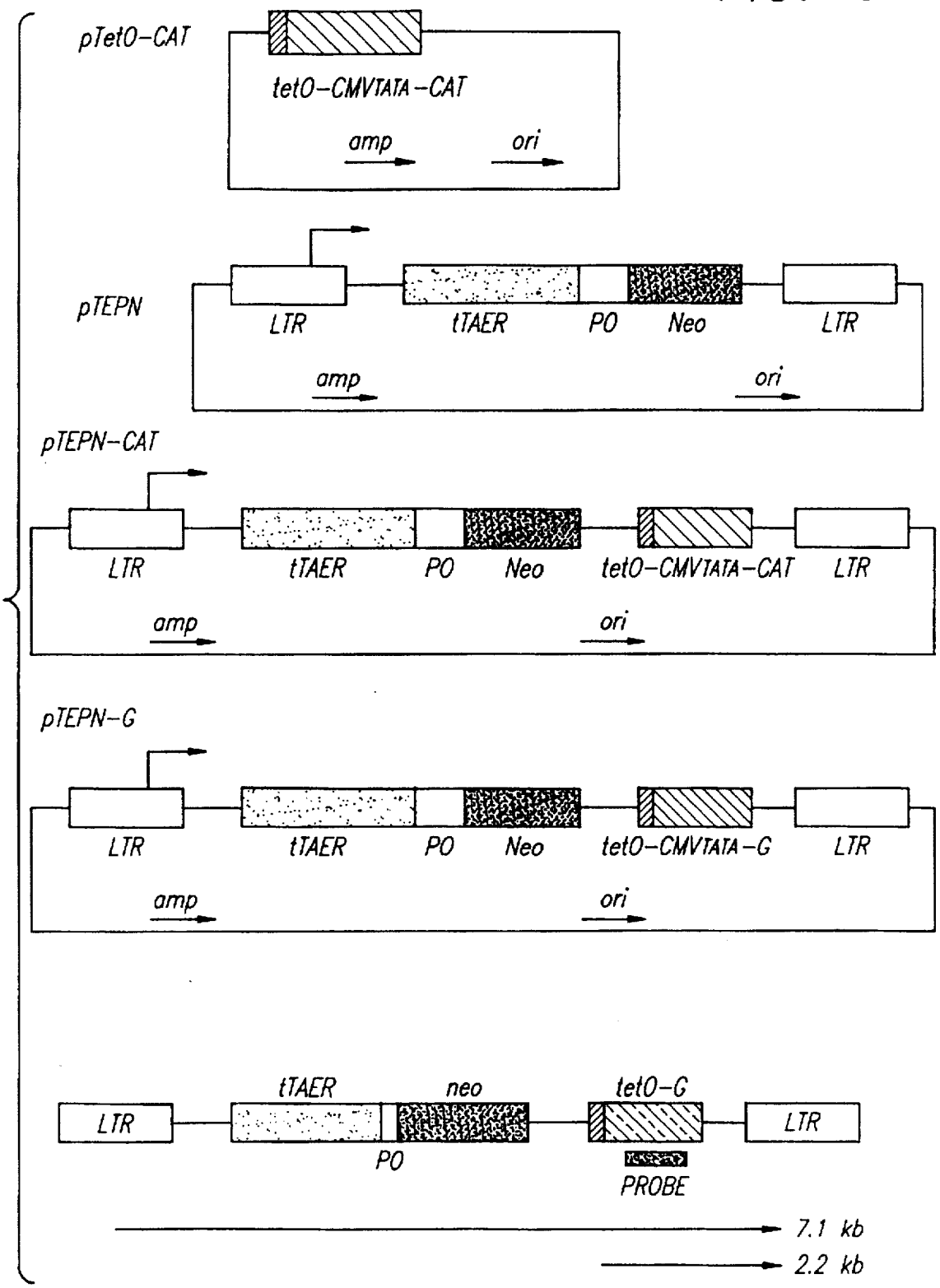
FIG. 6 is a schematic illustration of the constructs pTetO-CAT, pTEPN, pTEPN-CAT, and pTEPN-G. tetO represents a minimal CMV immediate early gene promoter linked to seven tandem copies of the tetR binding site; CAT, the bacterial chloramphenicol acetyltransferase gene; LTR, the long terminal repeat of MoMLV; tTAER, the gene encoding tTAER; PO, the internal ribosome entry site of poliovirus; neo, the gene encoding the neomycin phosphotransferase; G, the VSV G gene. Arrows above the LTRs indicate the approximate positions of transcriptional initiation sites; the plasmid maps are not drawn to scale.

The construct pLFIXRNL (FIG. 5) was generated by replacing the lacZ gene in pLZRNL with a 1.5-kb EcoRI DNA fragment containing the canine factor IX cDNA (FIX) isolated from pLNCdFIX (Roman et al., 1992 Somat. Cell Genet. 18:247–258). The pLTK-FIX construct (FIG. 5) was generated by ligating a 1.5-kb EcoRI DNA fragment containing the canine factor IX cDNA (FIX) from pLNCdFIX (Roman et al., 1992 Somat. Cell Genet. 18:247–258) to the 3' end of a 0.2-kb XbaI DNA fragment containing the HSV TK promoter linked to four copies of the BIII enhancer of the tyrosine aminotransferase gene from ptat-TKCAT (Boshart et al., 1990 Cell 61:905–916. The 3' end of the FIX-encoding fragment was ligated to the 5' end of a 71cb XhoI-SalI DNA fragment from LPONL (Yee et al., 1994, supra). The pTEPN-CAT construct (FIG. 6), which contains both the gene encoding tTAER and tetO, a promoter inducible by tTAER, the 1.9-kb XhoI-XbaI DNA fragment containing the TetO-CAT cassette was isolated from pTetO-CAT and was inserted at the unique XhoI site immediately downstream of the gene encoding neomycin phosphotransferase (neo) gene in pTEPN (FIG. 6). The pTEPN-G plasmid (FIG. 6) was similarly constructed by inserting the 2.1-kb XhoI DNA fragment containing the TetO-G cassette isolated from pTetO-G-1 into the unique XhoI site in pTEPN.

Example 2
Generation of Packaging Cell Lines

A variety of cell lines from different species were screened for their suitability as packaging cell lines that inducibly express a desired envelope protein according to the invention. The following cell lines were used:

| Source | Cell Line | ATCC No. |
|---|---|---|
| Human | HeLa | CCL 2 |
| | HT1080 | CCL 121 |
| | 293 | CRL 1573 |
| Canine | Cf2Th | CRL 1430 |
| | D17 | CCL 183 |
| | MDCK | CCL 34 |
| Hamster | BHK | CCL-10 |

Each of these cell lines was co-transfected with the plasmids pCMV-gag-pol, which expresses the MuLV Gag and Pol proteins from a minimal CMV promoter and pUT507, which expresses the phleomycin resistance gene. pCMV-gag-pol was constructed by inserting a 5.5 kb DNA fragment encoding the MoMLV gag-pol (nucleotide 621–5837, RNA Tumor Viruses, Vol. II, Cold Spring Harbor Lab., 1985) into the SalI site of the pCMV-BAM (Yee et al., supra). The cells were selected for phleomycin resistance and colonies were isolated.

Phleomycin-resistant clones were then tested for reverse transcriptase (RT) activity to determine whether the clones expressed an active retroviral Pol protein. The extracellular RT activity was measured using the standard assay of Goff et al. J. Virol. 38:239–248, 1981. Table 1 shows the results of the RT activity assay. Several clones of HT1080, Cf2Th, and Hela which showed high RT activity were isolated and used as gag-pol-expressing cells.

TABLE 1

| GP-Cell Line | | RT activity (cpm) | pLZRNL + pCMV-G Co-Transfection LZRNL titer[1] |
|---|---|---|---|
| CF2Th | GP #3 | 4,334 | 1–2% |
| | #4 | 6,003 | ~10% |
| | #6 | 6,098 | ~1% |
| Hela | GP #1 | 817 | ND[2] |
| | #5 | 635 | ND |
| | #6 | 566 | ND |
| HT1080 | GP #2-1 | 2,132 | ND |
| | GP #5-4 | 2,306 | ND |
| 293GP (+control) | | 7,934 | 5–10% |
| 293 (−control) | | 174 | ND |

[1]LZRNL titer is presented by the ratio (%) of the β-galactosidase positive (transduced) cells to negative (non-transduced) cells.
[2]ND stands for Not-Detected.

Example 3
Virus production by transient transfection of gag-pol-expressing cell lines with VSV G-encoding DNA Subcultures of each isolated gag-pol clone described in Example 2 were co-transfected with a retroviral plasmid pLZRNL (Xu et al., 1989, Virology 171:331–341), which expresses lacZ of E. coli, and with pCMV-G expressing VSV G. Two days after transfection, culture medium was harvested and used to infect indicator 208F cells to determine viral titers (Miyanohara et al., 1988, PNAS 85:6538–6542). Each 100 µl of harvested culture medium was applied to 208 F cells (approximately $5 \times 10^5$ cells in 6 cm dish) in the presence of Polybrene (4 µg/ml). Two days after infection, evidence of vector infection was examined by histochemical staining for expression of the transduced lacZ gene. The Cf2Th-gag-pol clone #4 (Cf2GP#4) was the highest producer of virus (Table 1).

Example 4
Establishment of Cf2Th cells stably-expressing tTAER

To establish stable tTAER-expressing clones, $5\times10^5$ Cf2ThGP#4 cells described above (Example 3) were transfected with 20 µg of phyg-CMV-tTAER, which contains the hygromycin-resistant gene under the control of the HSV TK promoter and the tTAER gene under control of the CMV promoter (FIGS. 4A–4C). Hygromycin-resistant Cf2ThGP#4/tTAER clones were isolated and expanded.

To test for stable tTAER expression, cells derived from the hygromycin-resistant clones were transfected with tetO-lux-containing construct pUHC13-3. The pUHC13-3 transfected cells were maintained in the presence or absence of tetracycline or 17 β-estradiol, and lux activity determined 48 hours after transfection. All clones responded to induction by tetracycline depletion with increased lux activity ranging from 2 to 90 fold when compared with that in tetracycline-containing medium. However, all clones responded negatively to the addition of 17β-estradiol. FIG. 5 shows the results of two typical clones (#8 and #17). Although the mechanism through, which 17β-estradiol induction caused negative induction in the Cf2Th cells is not yet clear, the degree of induction by removal of tetracycline is very high. Thus, the Cf2Th cell line containing the inducible expression system provides the surprising advantage that 17β-estradiol is not required for production of pseudotyped retroviruses.

Example 5
Production of Cf2Th packaging cell lines that inducibly express VSV G The Cf2Th clone that generated the highest viral titers in Example 3 (Cf2Th#4) was chosen for the introduction of pTetO-G-2 for inducible expression of VSV G. Approximately $5\times10^5$ Cf2ThGP#4/tTAER clone #17 cells described above were transfected with 20 µg of pTetO-G-2 (FIG. 5). Puromycin-resistant colonies were picked and expanded. The Cf2ThGP#4/tTAER/G cells were maintained in DMEM containing 10% FCS, 1 µg/ml tetracycline, 3 µg/ml puromycin and 400 µg/ml hygromycin. Approximately one-third of these puromycin-resistant clones failed to survive serial passage even in the presence of tetracycline, probably due to high basal levels of VSV-G expression.

Puromycin-resistant clones were screened for inducible VSV-G expression by FACS analysis. Cells derived from each clone were harvested after 60 hr incubation in the medium with or without tetracycline (1 µg/ml) and the levels of cell surface VSV-G expression were determined by reacting the cells with the monoclonal anti-VSV-G antibody I1 (provided by John Holland, University of California at San Diego), staining with the fluorescein isothiocyanate-conjugated goat anti-mouse immunoglobulins (Biosource), and analyzing the stained cells by flow cytometry as described previously (Burns et al., 1993 proc. Natl. Acad. Sci. USA 90:8033–8037).

Figure 7:
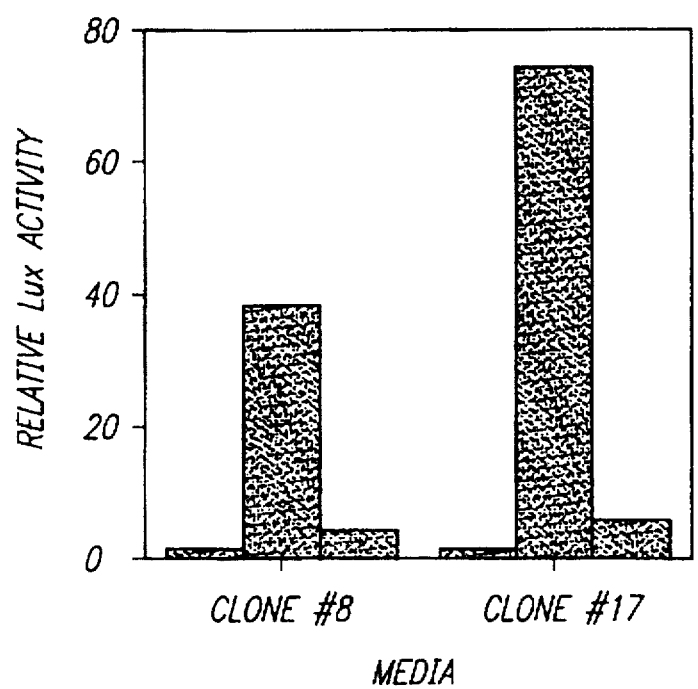
FIG. 7 is a graph showing tetracycline-regulated expression of the lux gene by the multi-chimeric transactivator tTAER in Cf2Th cells.
Figure 8:
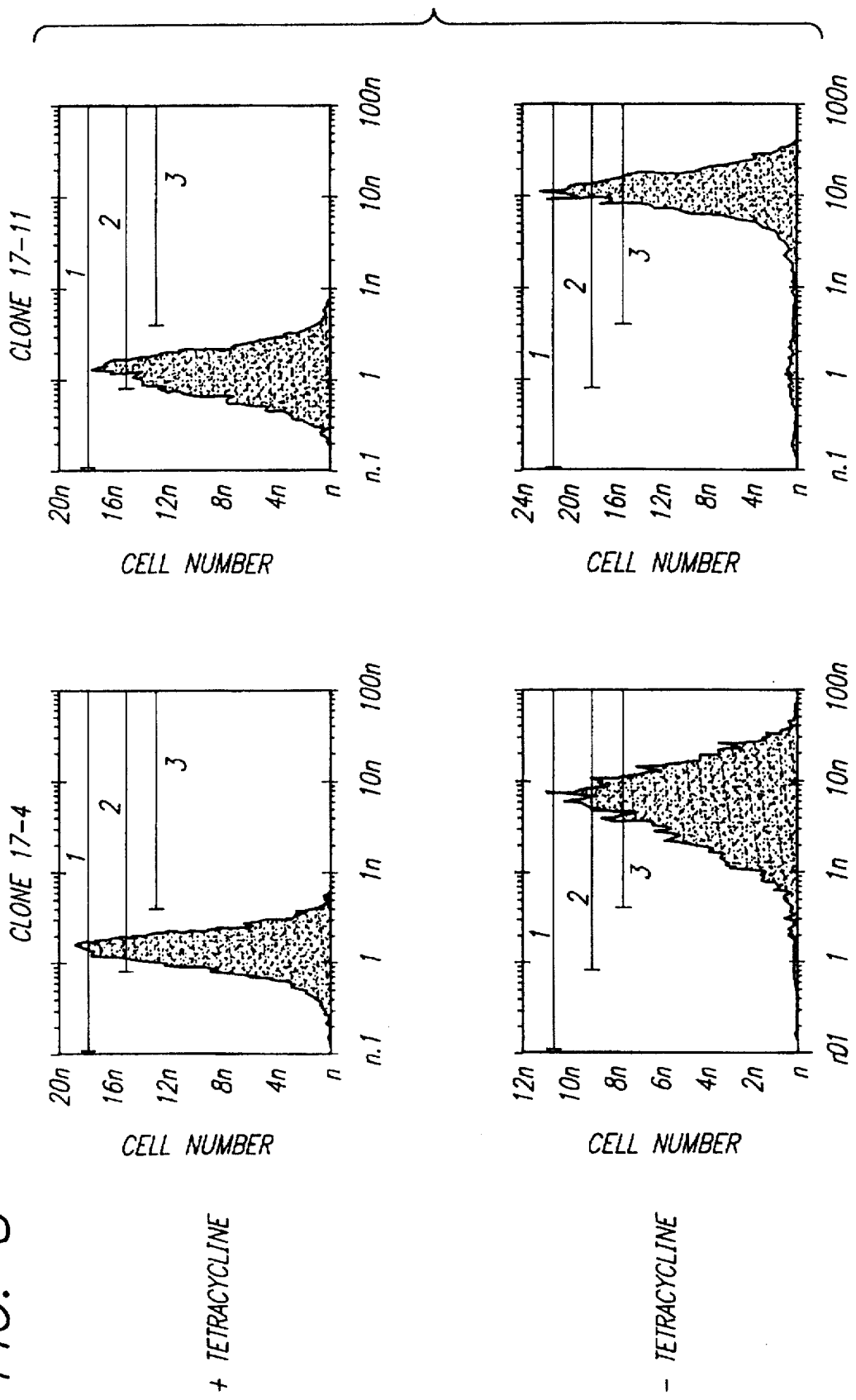
FIG. 8 is a set of four graphs showing flow cytometric analysis of inducible cell surface VSV G expression in two Cf2Th/tTAER/G clones.

FIG. 8 shows cell surface expression of VSV-G of two independent clones (#17-4 and #17-11) in the presence or absence of tetracycline. Both clones showed clear induction pattern of VSV-G expression by removing tetracycline from the medium. The levels of VSV-G expression on the cell surface are in good agreement with the levels of Lux expression shown in FIG. 7.

Example 6
Inducible production of VSV-G pseudotyped retroviral vectors from Cf2Th/tTAER/G cells Cells derived from clones 17-4 and 17-11 described above in Example 5 were infected with a retroviral vector LZRNL (Xu et al.) containing both the *E. Coli* lacZ and the neomycin-resistant gene (FIG. 5). After two weeks of G418 selection, the G418-resistant colonies were pooled and the levels of *E. coli* lacZ expression were determined by histochemical staining. Almost 100% of the G418-resistant cells were positive for transduced lacZ gene expression.

Pseudotyped virus was generated from the LZRNL virus-infected clone 17-4 and clone 17-11 cells by growing the cells in tetracycline-containing medium to a confluence of approximately 90%. The cells were then washed and the medium was changed to tetracycline-free medium. The pseudotyped virus was collected daily and the titer of the virus determined by selection of infected rat 208F cells in G418-containing medium. Virus stocks were tested for the presence of replication-competent helper retrovirus (RCR) by first amplifying the virus stocks in NIH3T3 cells (ATCC CCRL 1658; grown in high-glucose DMEM/10% FCS) for two weeks, and testing for the presence of RCR using the marker rescue assay in HT1080/LSHL cells(grown in high glucose DMEM/10% FCS) as described (Yee et al., 1994, supra).

The LZRNL virus produced from the infected clone 17-4 and 17-11 cells was harvested following 3 and 4 days incubation in tetracycline-free medium and the virus titers determined by infection of rat 208F cells as described above, followed by selection for G418-resistant colonies. As shown in Table 2, virus production increased in both clones upon removal of tetracycline. The virus titers generated from both Cf2Th clones were similar.

TABLE 2

Table 2 Inducible generation of the pseudotyped LZRNL virus virus titer (cfu/ml)*

| | days after induction (removal of tetracycline) | | |
|---|---|---|---|
| | 0 | 3 | 4 |
| clone 17.4 | $<1 \times 10^3$ | $6.4 \times 10^5$ | $1.0 \times 10^6$ |
| clone 17-11 | $<1 \times 10^3$ | $5.3 \times 10^5$ | $1.0 \times 10^6$ |

*The virus was harvested 0, 3 and 4 days after induction (removal of tetracycline) and the titer was determined by infection of rat 208F cells and selection for G418-resistant colonies.

The fact that both clones produce a very low level of virus ($<1 \times 10^3$ cfu/ml) in the presence of tetracycline and can be maintained for more than six months in culture indicates that Cf2Th cells can tolerate low levels of VSV-G expression and/or that tetracycline mediated regulation of VSV-G expression is very tight. Upon induction, high levels of VSV-G expression led to the high production of virus in both clones. This high induction is achieved by removing the tetracycline and did not require the addition of β-estradiol.

Example 7
Duration of VSV-G pseudotyped retroviral production from Cf2ThGP/tTAER/G packaging cells Since tetracycline removal induces not only virus production but also VSV-G accumulation in the cells that inevitably leads to cell death, it is important to determine the duration of virus production from the producer cells upon induction. Cells derived from clone 17-4 or clone 17-11 were infected with the LZRNL virus and selected for G418 resistance. The G418-resistant colonies were pooled and incubated in the medium with or without tetracycline for a week. The medium of the pooled cells was changed every 24 hr, and the titer of the accumulated virus was determined at the time indicated by infection of rat 208F cells followed by selection in G418-containing medium. Similar procedures were used to determine the duration of virus production from the pooled pLFIXRNL virus-infected clone 17-11 cells.

Culture medium from pooled virus-infected clones were collected over a period of 7 days. As shown in Table 3, the virus titers from all clones increased from <$10^3$ cfu/ml to over $10^6$ cfu/ml, which peaked at days 3 to 6 after induction.

Example 9
Inducible expression of the luciferase gene using the tTAER inducible expression system The transactivation function of tTAER was tested by co-transfecting human 293GP kidney cells (293GP cells) with pCMV-tTAER and pUHC13-3, which contains the

TABLE 3

Inducible Production of the Pseudotyped LZRNL and LFIXRNL viruses

| cell line | virus titer (cfu/ml) days after induction | | | | | | |
|---|---|---|---|---|---|---|---|
| | 1 | 2 | 3 | 4 | 5 | 6 | 7 |
| clone #4/LZRNL | <$1.0 \times 10^3$ | $4.0 \times 10^3$ | $4.5 \times 10^4$ | $6.4 \times 10^5$ | $3.5 \times 10^6$ | $3.0 \times 10^6$ | $1.6 \times 10^6$ |
| clone #11/LZRNL | <$1.0 \times 10^3$ | $1.0 \times 10^4$ | $9.0 \times 10^5$ | $2.0 \times 10^6$ | $2.0 \times 10^6$ | $7.5 \times 10^5$ | $9.0 \times 10^4$ |
| clone #11/LFIXRNL | <$1.0 \times 10^3$ | $1.3 \times 10^6$ | $2.0 \times 10^6$ | $2.7 \times 10^6$ | nd | $2.8 \times 10^6$ | $1.4 \times 10^6$ |

The high titer vector production was accompanied by an increase in the number of apparently dead cells, which is most likely due to the accumulation of high levels of VSV-G after induction. Nevertheless, prompt response to the induction and high level of vector production over a week is the big advantage of the Cf2Th derived inducible clones.

Example 8
Comparison of viral titers produced by transient transfection method to viral titers produced using the inducible expression system of the invention Using the pLFIXRNL construct, the transient transfection method of virus production was compared to virus production using the stable packaging cell lines 17-11. Transient transfection was accomplished by co-transfecting the pLFIXRNL construct with pCMV-G (which expresses VSV G from the CMV immediate early gene promoter) into Cf2ThGP#4 cells using the method of calcium phosphate co-precipitation (Graham et al., 1973 Virology 52:456–467). Three days after transfection, the virus was harvested. A Cf2ThGP#4/pLFIXRNL clone produced by the transient transfection method produced the pLFIXRNL virus at a titer of $1 \times 10^6$ cfu/ml. The virus titer produced by this method peaked at day 2 or 3 after transfection and decreased significantly at day 4.

In contrast, using the same LFIXRNL vector construct, virus with a titer of over $10^6 \times 10^6$ cfu/ml was generated from a pooled population of virus-producing clone #17-11 cells for over a week after induction. Not only does this latter approach has the advantage of avoiding the time-consuming step of identifying high producer clones, it is likely, as in other retrovirus production methods, that the isolation of optimal producer clones would result in even higher virus titers. The virus production studies were done by using the pooled infected cells. Since the Cf2Th clones identified and characterized here are not necessarily optimal producer clones, it is likely that Cf2Th clones providing even higher titus can be obtained. Since the inducible system does not require transient DNA transfection for virus production and the Cf2Th cells grow like regular fibroblasts and attach to the culture containers very well, many advanced cell culture technologies are easily applicable. For example, roller bottles can be used for mass production of pseudotyped vector using Cf2Th derived inducible cell lines. In contrast, 293GP cells are more difficult to grow and can not take advantage of such techniques. Thus, the packaging cell lines described herein are useful in large-scale production of clinical-grade virus especially appropriate for studies aimed at human gene therapy.

firefly lux gene under the control of a minimum promoter linked to seven tandem copies of tetO (Gossen et al., 1992, supra). The human 293GP kidney cell line expresses the Gag and Pol proteins of MoMLV and has been described previously (Burns et al., 1993 Proc. Natl. Acad. Sci. USA 90:8033–8037; PCT published application no. WO 92/05266, published Apr. 2, 1992, each of which are incorporated herein by reference for preparation of constructs encoding the Gag and Pol proteins of MoMLV (especially the construct pSVgp, which provides for expression of MoMLV Gag and Pol proteins) and generation of the 293GP cell line, which contains the pSVgp construct and is derived the human kidney cell line 293 (ATCC CRL 1573)). Transfection was performed by the method of calcium phosphate co-precipitation (Graham et al., 1973 Virology 52:456–467). The 293GP cells containing tTAER (293GP/tTAER) were maintained in Dulbecco's modified essential medium (DMEM) containing 10% fetal calf serum (FCS), 1 µg/ml tetracycline, 1 µg/ml puromycin, and 800 µg/ml hygromycin.

Figure 9:
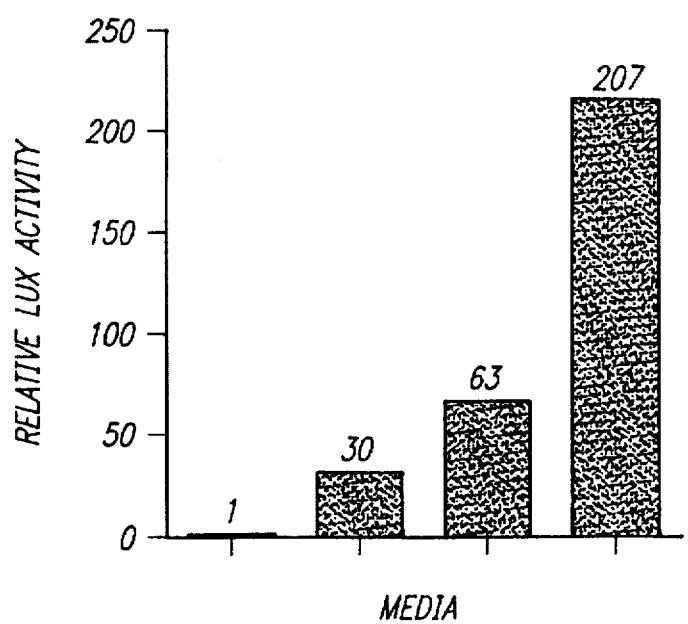
FIG. 9 is a graph showing inducible expression of the lux gene by the multi-chimeric transactivator tTAER.

VSV-G expression was induced by removing the tetracycline-containing medium, washing the cells twice with DMEM with at least 30 min incubation in DMEM between washes. The cells were then maintained in DMEM/ 10% FCS containing β-estradiol at a concentration of 2 µM. Luciferase (lux) activity was detected in cell extracts prepared by subjecting the cells to three cycles of freeze-thawing in lysis buffer (0.1M potassium phosphate/1 mM dithiothreitol, pH 7.8), followed by centrifugation at room temperature for 3 min to remove cell debris. Lux activity was determined as described (de Wet et al., 1987 Mol. Cell. Biol. 7:725–737). The results of these experiments are shown in FIG. 9. The numbers above the bars in the graph represent the relative fold induction by normalizing the lux activity of each condition to that of tetracycline-containing medium which was arbitrarily set as 1. The data are the average of two independent experiments.

Removal of tetracycline or addition of tetracycline plus 17β-estradiol activated lux expression; however, maximum lux expression was observed only after simultaneous removal of tetracycline and addition of β-estradiol (FIG. 9). The observation that tTAER requires 17β-estradiol for its maximum induction activity in 293GP cells indicates that the VP16 transactivation function is regulated by the ER ligand-binding domain of tTAER. In addition, the negative effect of the VP16 activation domain upon general cellular transcription (i.e., the "squelching" effect) is also regulated by the ER ligand-binding domain in tTAER, which allows for increased efficiency in the isolation of tTAER-expressing cell lines in the absence of 17β-estradiol.

In contrast to the reported difficulty of establishing stable clones expressing tTA (Shockett et al., 1995 *Proc. Natl. Acad. Sci. USA* 92:6522–6526), the relative ease of establishing stable clones expressing tTAER in this study indicates that the current system is advantageous for the inducible expression of the tet regulatory elements and other potentially toxic gene products.

Example 10
Expression of tTAER from a retroviral vector

The bicistronic retroviral vector, pTEPN, was constructed with the tTAER gene followed by the internal ribosome entry site derived from the poliovirus genome and the neomycin phosphotransferase gene (neo) (FIG. 6). Expression of both genes was under the control of the MoMLV 5' long terminal repeat (LTR). Human HT1080 fibrosarcoma cells (ATCC CCL 121) were co-transfected with pTEPN and with pTetO-CAT, which contains the CAT gene controlled by tetO, which is composed of a minimal promoter of the CMV immediate early gene linked to seven tandem copies of the tetR-binding site (FIG. 6).

Figure 10:
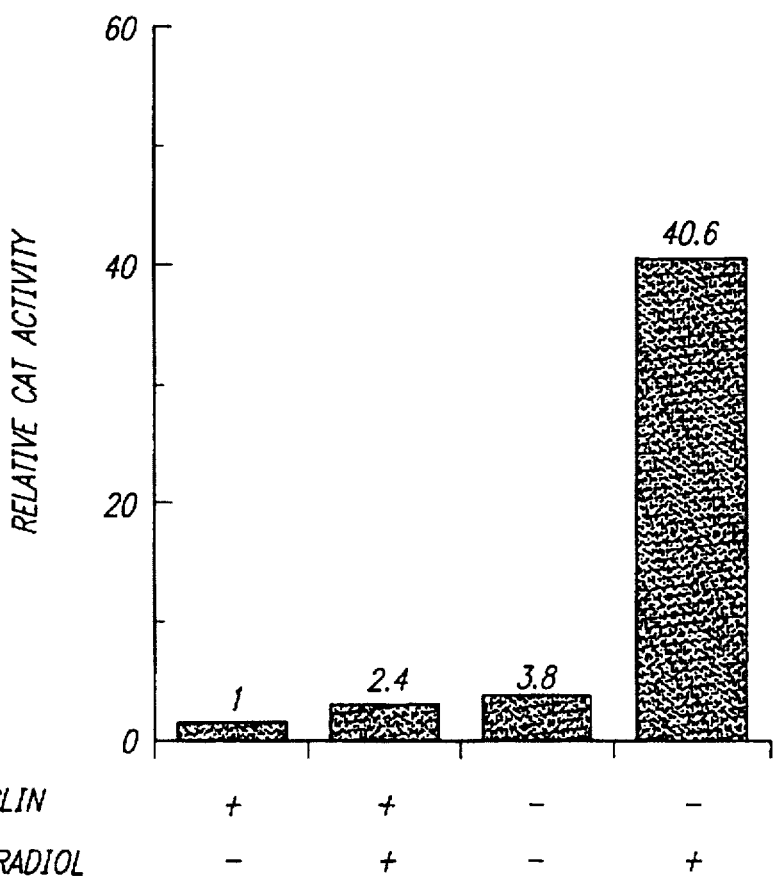
FIG. 10 is a graph showing inducible expression of CAT activity as regulated by the multi-chimeric transactivator tTAER.

G418-resistant HT1080 cells were routinely maintained in 1 µg/ml tetracycline and 800 µg/ml G418-containing medium. Tetracycline was removed by washing the cells with medium containing no tetracycline and incubating the cells at 37° C. for 30 minutes. The washing procedure was repeated a minimum of three times. For induction of gene expression, cells were incubated in phenol red-free DMEM containing 10% charcoal/dextran-treated fetal calf serum and 2 µM 17β-estradiol for 72 hours before the cell extract was prepared. Approximately 48 hours after transfection, CAT activity was determined by the method of Sleigh (Sleigh, M. J. 1986 *Anal. Biochem.* 156:251–256). A 100 µl sample of reaction mixture contained 150 mM Tris-HCl (pH7.8), 1.6 mM chloramphenicol, 90 µM acetyl coenzyme A (Pharmacia), 1 µCi [$^{14}$C]acetyl coenzyme A (Amersham; 60 mCi/mmol), and 10 µl of cell extract. The mixture was incubated at 37° C. for 60 minutes, and the labeled chloramphenicol was quantitated by liquid scintillation counting after extraction into the ethyl acetate layer. Protein concentration was determined by the method of Bradford (Bradford, M. D. 1976 *Anal. Biochem.* 72:248–254). The results of these experiments are shown in FIG. 10. The numbers above the bars in the graph represent the relative fold induction by normalizing the CAT activity of each condition to that of tetracycline-containing medium which was arbitrarily set as 1.

As shown in FIG. 10, CAT expression was not activated in the presence of tetracycline alone or tetracycline plus the estrogen analog 17β-estradiol, consistent with the model that tTAER cannot bind DNA in the presence of tetracycline. In contrast to the transactivation function of tTA, tTAER failed to activate the CAT expression upon the removal of tetracycline from the culture medium. CAT expression was strongly activated only when tetracycline was removed and 17β-estradiol was added to the culture medium. These results again demonstrate that the transactivation function of VP16 in tTAER is modulated by the ER ligand binding domain in cis, and the activity of tTAER is under the control of both tetracycline and 17β-estradiol.

Example 11
Establishment of 293GP cells stably-expressing tTAER

To establish stable tTAER-expressing clones, 5×10$^5$ 293GP cells, which express the MoMLV Gag and Pol proteins (Yee et al., 1994, supra), were transfected with 20 µg of phyg-CMV-tTAER, which contains the hygromycin-resistant gene under the control of the HSV TK promoter and the tTAER gene under control of the CMV promoter (FIG. 5). Thirty hygromycin-resistant colonies were picked and expanded.

To test for stable tTAER expression, cells derived from these thirty clones were transfected with tetO-lux-containing construct pUHC13-3. The pUHC13-3 transfected cells were maintained in the presence of tetracycline or β-estradiol, and lux activity determined 48 hours after transfection. All 30 clones responded to β-estradiol induction with increased lux activities ranging from 2 to 90 fold when compared with that in tetracycline-containing medium. This result is consistent with the prediction that tTAER is less toxic than tTA and that stable cell lines expressing tTAER can thus be established more readily.

Example 12
Establishment of 293GP packaging cell lines for VSV-G pseudotyped retroviral vectors The clone which generated the highest induction level of the lux activity in Example 9 was chosen for the introduction of pTetO-G-2 for inducible VSV-G expression. Approximately 5×10$^5$ 293GP/tTAER cells described above were transfected with 20 µg of pTetO-G-2 (FIGS. 4A–4C). Approximately 70 puromycin-resistant colonies were picked and expanded. The 293GP/tTAER/G cells were maintained in DMEM containing 10% FCS, 1 µg/ml tetracycline, 1 µg/ml puromycin and 800 µg/ml hygromycin. Approximately one-third of these puromycin-resistant clones failed to survive serial passage even in the presence of tetracycline, probably due to high basal levels of VSV-G expression.

The remaining puromycin-resistant clones were screened for inducible VSV-G expression by immunoblot assay. Approximately 1×10$^5$ cells derived from each clone were harvested after 48 hr incubation in medium containing either 1 µg/ml tetracycline or 2 µM β-estradiol and the cells were lysed in a 25 µl of buffer containing 50 mM Tris-HCl (pH7.5), 150 mM NaCl, 1% Nonidet P-40, 0.5% deoxycholic acid and 0.1% SDS. One µl of extract was spotted on a nylon membrane (Micron Separation Inc.) and VSV-G protein was detected by the ECL Western blotting system (Amersham) with the I1 monoclonal antibody specific for VSV G (provided by John Holland, University of California at San Diego). β-estradiol-inducible VSV-G expression was confirmed in 34 clones.

Inducible expression of the VSV-G gene by β-estradiol was confirmed by examining VSV-G mRNA expression in two 293GP/tTAER/G clones (clones 13 and 21). Briefly, parental 293GP/tTAER cells (negative control) and from two 293GP/tTAER/G clones (clones 13 and 21) were grown in the presence of tetracycline or β-estradiol and total RNA isolated according to the procedure of Chomczynski and Sacchi (Chomczynski et al., 1987 *Anal. Biochem.* 162:156–159). mRNA was isolated using the polyATract mRNA isolation system (Promega), separated on a 2.2M formaldehyde/1% agarose gel, and transferred to a nylon membrane (Micron Separation Inc.). The membrane was hybridized with $^{32}$P-labeled probes prepared by the random primed DNA labeling kit (Boehringer Mannheim). The probe for VSV-G was derived from a 1.6-kb BamHI DNA fragment of pCMV-G containing the VSV-G gene (FIG. 6; Yee et al., 1994, supra). The probe for rabbit β-actin was derived from a 2-kb PstI DNA fragment of pUCA1 (Cleveland et al., 1980 *Cell* 20:95–105).

The VSV-G mRNA in clone 13 was faintly detectable in the presence of tetracycline. Upon β-estradiol induction, the level of the VSV-G mRNA increased dramatically. In contrast, the VSV-G mRNA in clone 21 was undetectable in the presence of tetracycline, but became detectable upon β-estradiol induction. Consistent with the levels of the VSV-G mRNA, β-estradiol induction of clone 13 led to severe cytopathic effects and cell death within 4 days whereas the cell morphology of clone 21 remained relatively normal under the same conditions.

Example 13
Inducible production of VSV-G pseudotyped retroviral vectors from 293GP/tTAER/G cells Cells derived from clones 13 and 21 described above in Example 12 were infected with a retroviral vector LTK-FIX containing both the canine Factor IX cDNA and the neomycin-resistant gene under the control of the HSV TK promoter (FIG. 5). The retroviral vector LTK-FIX was generated by transfection of 20 µg of pCMV-G into 293GP cells harboring plasmid pLTK-FIX. The virus was harvested 60 hours after DNA transfection and the resulting virus was used to infect clone 13 and 21. After two weeks of G418 selection, the G418-resistant colonies were pooled and the level of cell surface VSV G expression determined by reacting the cells with the monoclonal anti-VSV-G antibody I1, staining with the fluorescein isothiocyanate-conjugated goat anti-mouse immunoglobulins (Biosource), and analyzing the stained cells by flow cytometry, as described previously (Burns et al., 1993 *Proc. Natl. Acad. Sci. USA* 90:8033–8037).

Figure 11:
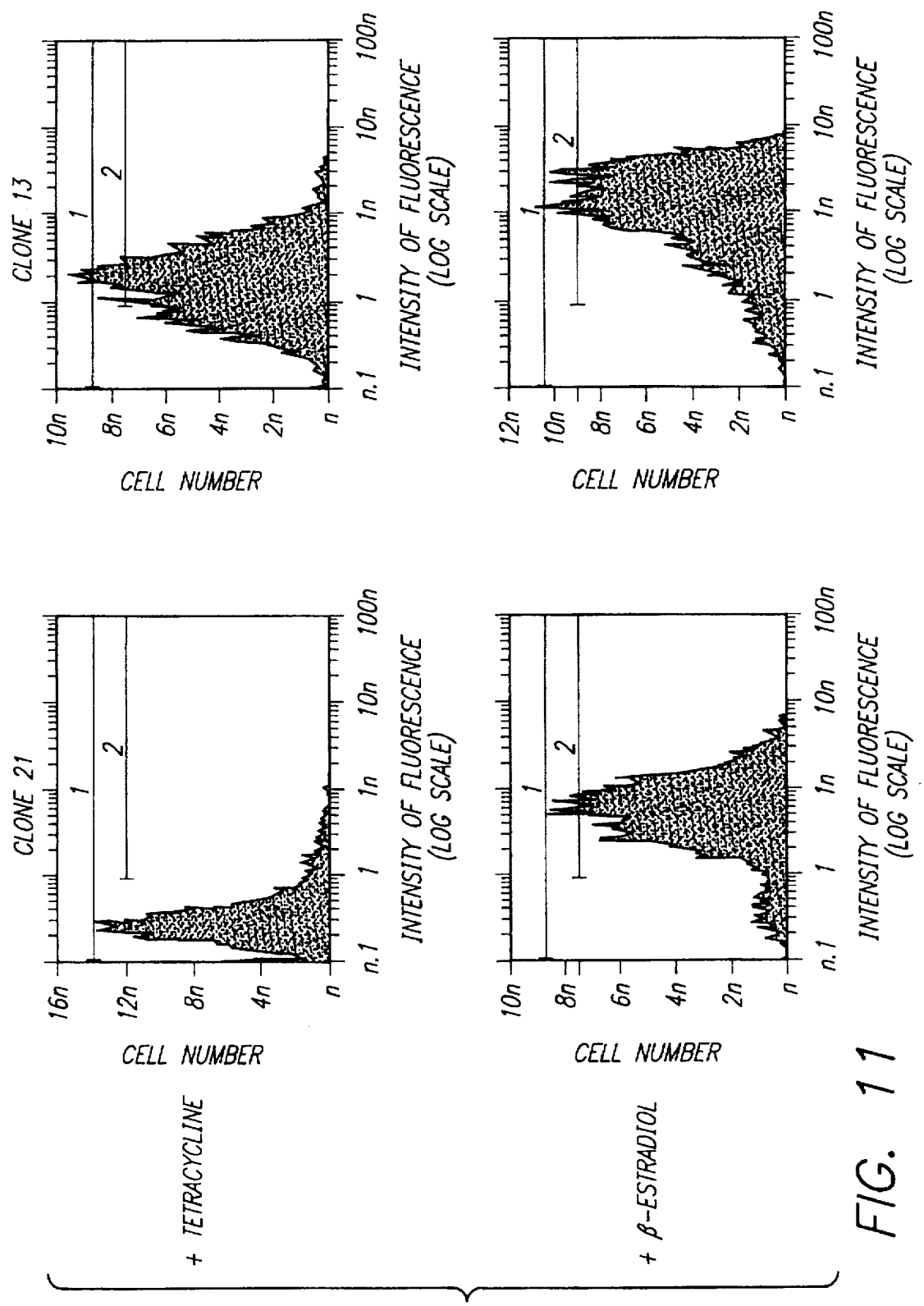
FIG. 11 is a set of four graphs showing flow cytometric analysis of inducible cell surface VSVG expression in pooled LTK-FIX virus-infected 293GP/tTAER/G clones.

As shown in FIG. 11, cell surface expression of VSV-G was undetectable in LTK-FIX virus-infected clone 21 cells in the presence of tetracycline and was induced upon the removal of tetracycline and the addition of β-estradiol. In contrast, a significant level of VSV-G expression was detected in the LTK-FIX virus-infected clone 13 cells even in the presence of tetracycline and the level of VSV-G was increased further upon β-estradiol induction. The levels of VSV-G on the surface of cells in the presence of tetracycline or β-estradiol is in good agreement with the level of VSV-G mRNA in these two clones under the same conditions (see Example 12).

Example 14
Production of VSV-G pseudotyped retroviral particles containing LTK-FIX-encoding RNA from 293GP/tTAER/G packaging cells Pseudotyped virus was generated from the LTK-FIX virus-infected clone 13 and clone 21 cells by growing the cells in tetracycline-containing medium to a confluence of approximately 90%. The cells were then washed and the medium was changed to tetracycline-free medium with or without β-estradiol as described above. The pseudotyped virus was collected at different times (e.g., 48 hours, and/or 2, 4, 6, and 8 days post-infection) and the titer of the virus determined by selection of infected rat 208F cells in G418-containing medium. Virus stocks were tested for the presence of replication-competent helper retrovirus (RCR) by first amplifying the virus stocks in NIH3T3 cells (ATCC CCRL 1658; grown in high-glucose DMEM/10% FCS) for two weeks, and testing for the presence of RCR using the marker rescue assay in HT1080/LSHL cells(grown in high glucose DMEM/10% FCS) as described (Yee et al., 1994, supra).

The LTK-FIX virus produced from the infected clone 13 and 21 cells was harvested following 48 hr incubation in tetracycline- or β-estradiol-containing medium and the virus titers determined by infection of rat 208F cells as described above, followed by selection for G418-resistant colonies. As shown in Table 4, virus production increased in both clones upon β-estradiol induction. However, despite the fact that clone 13 expressed significantly more VSV-G upon induction, the virus titers generated from both clones were similar. This may be due to the cytopathic effect generated from overexpression of VSV-G in clone 13 cells upon β-estradiol induction (see below). The observation that clone 13-derived cells generated approximate 20 fold more virus than clone 21-derived cells in the presence of tetracycline is consistent with the higher basal levels of VSV-G expressed in clone 13 cells under the uninduced condition (Example 12 and FIG. 11).

TABLE 4

Inducible generation of the pseudotyped LTK-FIX virus

| Cell Line | Virus Titer* (cfu/ml) | | Fold of Induction |
|---|---|---|---|
| | +tetracycline −17β-estradiol | −tetracycline +17β-estradiol | |
| clone 13 | $2.7 \times 10^3$ | $6.0 \times 10^4$ | 22 |
| clone 21 | $1.4 \times 10^2$ | $6.6 \times 10^4$ | 471 |

*The virus was harvested 48 hr after 17β-estradiol induction and the titer was determined by infection of rat 208F cells and selection for G418-resistant colonies.

The fact that clone 13 expresses detectable amounts of VSV-G in the presence of tetracycline and can be maintained for more than six months in culture indicates that human 293 cells can tolerate low levels of VSV-G expression. However, despite higher levels of VSV-G expression in clone 13 than that in clone 21 upon induction, the amounts of virus generated from the two clones are similar 48 hr after β-estradiol induction (Table 4 and FIG. 6). This may be attributed to the cytopathic effect observed in clone 13 after β-estradiol induction, an effect probably caused by the relatively high level of VSV-G expression. The toxicity of VSV-G is most likely the result of its expression on the cell surface which leads to syncytia formation. The levels of VSV-G expression in clones 13 and 21 correlate well with the observed degree of the cytopathic effect in these two clones after β-estradiol induction. This observation suggests that a lower level of VSV-G expression such as that in clone 21 cells may have the advantage of allowing the producer cells to survive for prolonged periods after β-estradiol induction, thereby producing more pseudotyped virus from the producer cells.

Example 15
Duration of VSV-G pseudotyped retroviral production from 293GP/tTAER/G packaging cells Since β-estradiol induces not only virus production but also VSV-G accumulation in the cells that inevitably leads to cell death, it is important to determine the duration of virus production from the producer cells upon induction. Cells derived from clone 21 or clone 13 were infected with the LTK-FIX virus and selected for G418 resistance. The G418-resistant colonies were pooled and incubated in DMEM (diamond), DMEM plus tetracycline (circle), or DMEM plus 17β-estradiol (square) for the period indicated in FIG. 12. The medium of the pooled cells was changed every 48 hr, and the titer of the accumulated virus was determined at the time indicated by infection of rat 208F cells followed by selection in G418-containing medium.

Culture medium from pooled LTK-FIX virus-infected clone 21 cells was collected over a period of 16 days. As shown in FIG. 9, the virus titers from the clone 21 cells remained at a low but constant level in the presence of tetracycline for the entire period. In contrast, induction with β-estradiol led to a gradual increase in clone 21 virus titers.

No cytopathic effect was observed until two weeks after β-estradiol induction, a delay that may be attributed to the relatively low level of VSV-G expression in clone 21-derived cells (Example 12 and FIG. 11).

Interestingly, in the absence of β-estradiol induction, the viral titers increased from $10^3$ cfu/ml to $4\times10^6$ cfu/ml over a period of two weeks after the removal of tetracycline (FIG. 12, clone 21). Mass cell death, accompanied by a reduction in virus titer, occurred after three weeks of incubation in this medium. The reason for the dramatic increase in virus titers remains unclear at the present time. To determine whether the increase in virus titers was due to the presence of helper virus contamination, the virus stocks collected from day 14 and day 16 after β-estradiol induction were amplified in NIH3T3 cells followed by a marker rescue assay as described above. No helper virus was detected using this assay.

Similar procedures were used to determine the duration of virus production from the pooled LTK-FIX virus-infected clone 13 cells (FIG. 12, clone 13). The virus titers increased approximately 100 fold two days after β-estradiol induction. However, the titers decreased with prolonged incubation in the presence of β-estradiol; this reduction was accompanied by an increase in the number of apparently dead cells. The increase in cell death is probably due to the accumulation of high levels of VSV-G after β-estradiol induction in this clone. Similar to the clone 21-derived cells, the titers of clone 13-derived cells in the absence of β-estradiol continued to increase for up to 8 days after the removal of tetracycline (FIG. 12).

The LTK-FIX virus titer from individually isolated G418-resistant colonies of the infected clone 21 cells has also been determined (Table 5). Removal of tetracycline and addition of β-estradiol for 60 hours resulted in an increase in the virus titer exceeding 3–4 orders of magnitude. Similar results were obtained with clone 13-derived cells (data not shown).

TABLE 5

The virus titers generated from independently isolated clones of LTK-FIX virus-infected clone 21 cells.

| Clone No. | Virus Titer* (Cfu/ml) | |
|---|---|---|
| | +tetracycline −17β-estradiol | −tetracycline +17β-estradiol |
| 1 | 81 | $5.9 \times 10^5$ |
| 2 | 36 | $5.2 \times 10^5$ |
| 3 | 100 | $2.7 \times 10^5$ |
| 4 | 24 | $2.4 \times 10^5$ |
| 5 | 111 | $0.8 \times 10^5$ |
| 6 | 71 | $2.0 \times 10^5$ |
| 7 | 24 | $0.9 \times 10^5$ |
| 8 | 34 | $5.7 \times 10^5$ |

*The virus was harvested 60 hr after 17β-estradiol induction from a 100-mm tissue culture dish containing 6 ml of culture medium. The virus titer was determined by infection of rat 208F cells and selection of G418-resistant colonies.

Example 16
Comparison of viral titers produced by transient transfection method to viral titers produced using the inducible expression system of the invention Using the LTK-FIX construct, the transient transfection method of virus production was compared to virus production using the stable packaging cell lines clone and clone 21. Transient transfection was accomplished by co-transfecting the LTK-FIX construct with pCMV-G (which expresses VSV G from the CMV immediate early gene promoter) into 293GP cells using the method of calcium phosphate co-precipitation (Graham et al., 1973 *Virology* 52:456–467).

Sixteen days after transfection, the virus harvested. A 293GP/LTK-FIX clone produced by the transient transfection method produced the LTK-FIX virus at a titer of $3\times10^6$ cfu/ml.

In contrast, using the same LTK-FIX vector construct, virus with a titer of $4\times10^6$ cfu/ml was generated from a pooled population of virus-producing clone 21 cells 48 hours after introduction of the TLK-FIX construct into the clone 21 cells. Not only does this latter approach of the invention have the advantage of avoiding the time-consuming step of identifying high producer clones, it is likely, as in other retrovirus production methods, that the isolation of optimal producer clones would result in even higher virus titers. Thus, the packaging cell lines described herein are useful in large-scale production of clinical-grade virus especially appropriate for studies aimed at human gene therapy.

Example 17
Production of VSV-G pseudotyped retroviral particles containing β-galactosidase-encoding RNA from 293GP/tTAER/G packaging cells The retroviral vector LZRNL (Yee et al., 1994, supra), which expresses β-galactosidase, was used infect 293GP/tTAER/G clones 13 and 21 to produce packaging cell lines using the methods described above for the production of LTK-FIX virus-producing cell lines. The LZRNL-producing 293GP/tTAER/G clone 13 and clone 21 producer cell lines exhibited viral titers similar to those of the LTK-FIX 293GP/tTAER/G clone 13 and clone 21 producer cell lines described above. These results demonstrate that clones 13 and 21 can serve as packaging cell lines for the production of VSV-G pseudotyped retroviral vectors.

Example 18
Production of HT1080 cells stably expressing tTAER

Figure 13:
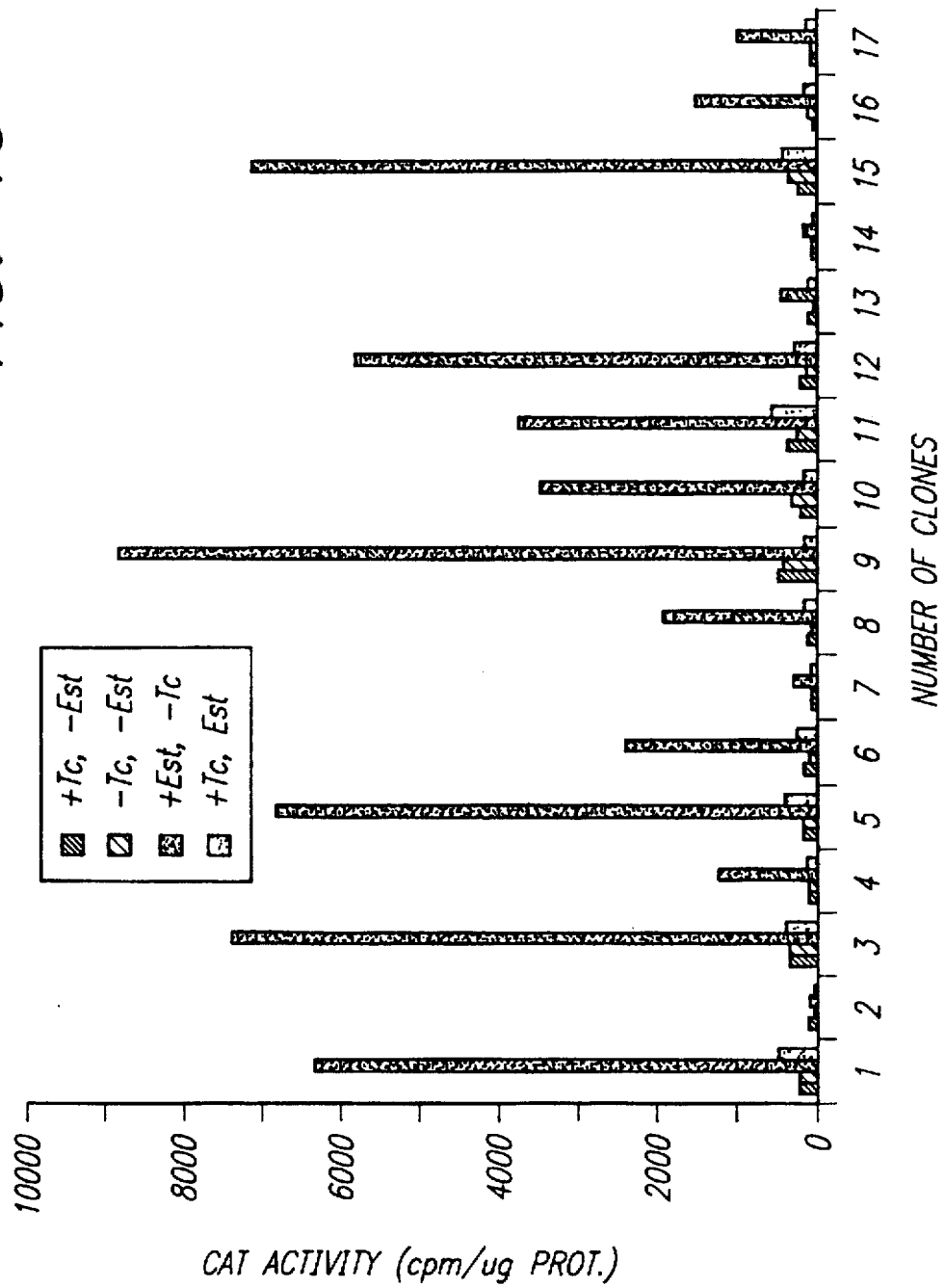
FIG. 13 is a graph showing inducible CAT expression in stable tTAER-expressing HT1080 cells containing the pTetO-CAT construct. Dark-striped bars, with tetracycline, no 17β-estradiol (+Tc, −Est); light-striped bars, no tetracycline, no 17β-estradiol (−Tc, −Est); solid boxes, with 17β-estradiol, no tetracycline (−Tc, +Est); open boxes, with tetracycline and 17β-estradiol (+Tc, +Est).

Infectious TEPN virus was generated by transfecting the pTEPN plasmid into 293GP cells using calcium phosphate co-precipitation (Graham et al. 1973, supra). Forty-either hours after transfection, infectious TEPN virus was harvested and used to infect HT1080 cells. Seventeen individual G418-resistant HT1080 colonies were picked and expanded. To test for the tTAER activity, plasmid pTetO-CAT was transfected into these clones and the CAT expression was determined 72 hours after transfection. As shown in FIG. 13, sixteen out of seventeen of the G418-resistant HT1080 clones exhibited CAT activity only when tetracycline was removed and phenol red-free DMEM containing 10% charcoal/dextran-treated fetal calf serum and 2 μM 17β-estradiol was added. The degree of induction varied from 3 to 40 fold (an average of 20 fold). Variation in the induction may reflect different levels of tTAER in each individual clones due to random retrovirus integration into the host cell chromosomes. These results demonstrate that the addition of the ER ligand-binding domain subjects the transactivation function of tTA under the regulation of estrogen. Moreover, since a majority of the isolated clones express tTAER, the toxicity associated with stable tTA expression is alleviated by the addition of the ER ligand-binding domain.

Example 19
Production of tTAER and inducible CAT expression from a single retroviral vector in HT1080 cells In addition to tTA toxicity, the tTA-based inducible system suffers from the fact that establishment of cell lines requires two steps and only those cell lines with good transfection efficiencies can readily be used. Thus, an inducible expression system of the invention was designed so that stable producer clones can be generated using a single retrovital construct in a single transfection step.

Figure 14:
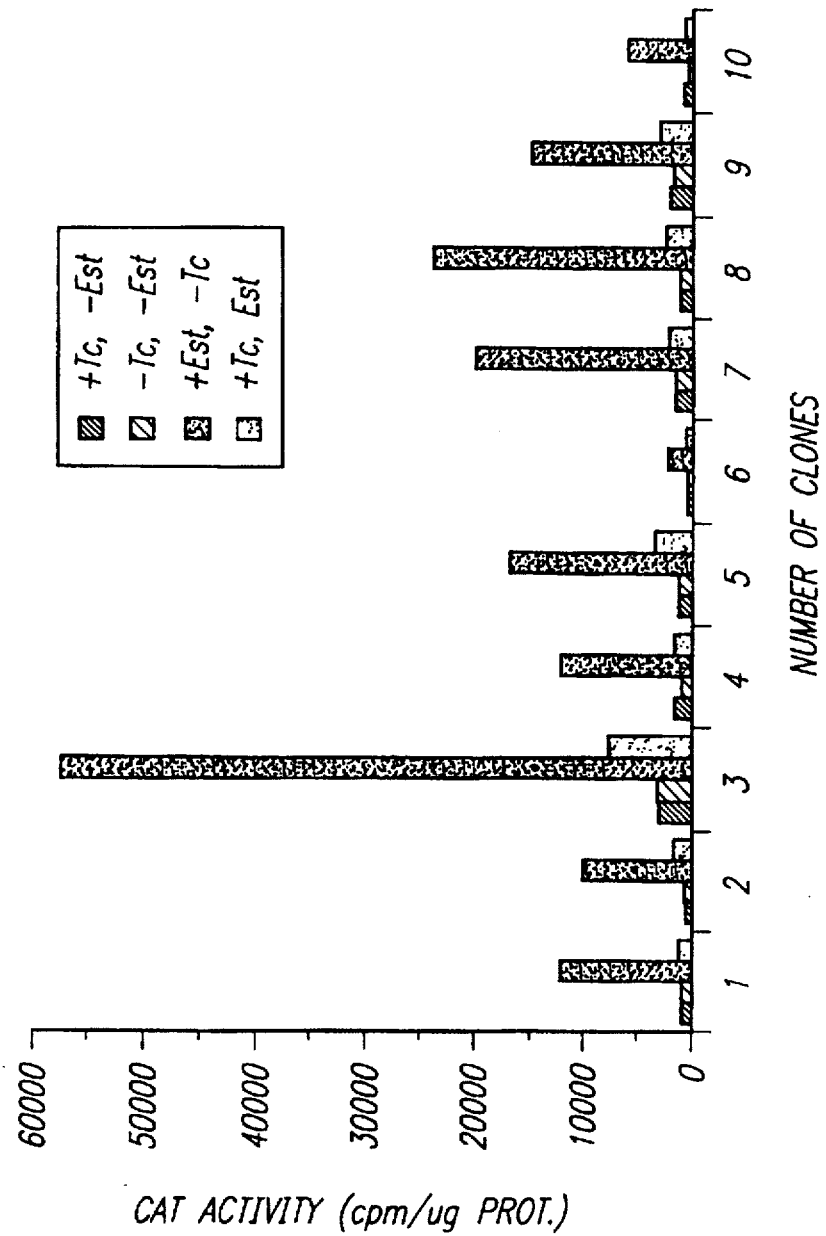
FIG. 14 is a graph showing inducible CAT expression in TEPN-CAT virus-infected HT1080 cells. Dark-striped bars, with tetracycline, no 17β-estradiol (+Tc, −Est); light-striped bars, no tetracycline, no 17β-estradiol (−To, −Est); solid boxes, with 17β-estradiol, no tetracycline (+Est, −Tc); open boxes, with tetracycline and 17β-estradiol, (+Tc, +Est).

The pTEPN-CAT construct (FIG. 6), which contains both the TetO-CAT cassette (inserted immediate downstream of the neogene in pTEPN) and the CMV-tTAER cassette was transfected into 293GP cells using calcium phosphate co-precipitation (Graham et al., 1973, supra). Forty-either hours after transfection, infectious TEPN-CAT virus was harvested and used to infect HT1080 cells. Twelve G418-resistant TEPN-CAT HT1080 clones were picked and expanded, and CAT expression tested as described above. In ten out of twelve TEPN-CAT HT1080 clones, CAT expression was activated only upon the removal of tetracycline and the addition of 17β-estradiol (FIG. 14). Induction of the CAT expression varied from 8 to 27 fold (an average of 15 fold). The two clones that failed exhibit 17β-estradiol-induced CAT expression expressed CAT activity at levels close to background under all conditions, possibly as a result of integration of the retroviral vector into a site unfavorable for gene expression or due to mutations introduced into the retrovital genome during the process of reverse transcription. These results demonstrate that this inducible gene expression system can be transduced into mammalian cells with high efficiencies via retroviral-mediated gene transfer. Moreover, the complete estrogen-inducible expression system including the tTAER gene and the target gene controlled by the inducible tetO promoter can be transduced into eukaryotic cells with a single retroviral vector.

Example 20

Inducible expression of VSV-G in HT1080 cells using the tTAER inducible system in a single retrovital vector The CAT gene in pTEPN-CAT was replaced with the VSV G gene to create the construct pTEPN-G. Infectious TEPN-G retroviral vectors were generated from 293GP cells transfected with pTEPN-G and used to infect HT1080 cells as described in Example 22. Inducible expression of VSV G with 17β-estradiol was confirmed in thirty out of thirty-five individually derived G418-resistant TEPN-G 293GP clones using immunoblotting analysis as described above.

Cell surface VSV G expression in five of these thirty clones TEPN-G 293GP clones was examined by flow cytometric analysis as described above. As shown in FIG. 15, seventy-two hours after the removal of tetracycline and the addition of 17β-estradiol, all five clones expressed significant levels of VSV G on the cell surface. In contrast, no VSV G expression was detected on the cell surface of these same clones when grown in tetracycline-containing medium.

To determine whether inducible VSV G cell surface expression is due to an increase in the level of the transcript initiated from the tetO-containing promoter in the TEPN-G virus, clone 24 was grown in tetracycline- or 17β-estradiol-containing medium, and mRNA isolated and analyzed by Northern blot analysis. Northern blot analysis was performed as described above, except that the probe for the VSV G gene was derived from a 1-kb KpnI fragment, of pTetO-G-1 (FIG. 5).

Both the 7.1-kb retroviral genomic transcript initiated from the 5'LTR and the 2.2-kb transcript initiated from the tetO-containing promoter were detectable with the VSV G gene probe in cells grown in tetracycline-containing medium (see FIG. 6 for the relative positions of the 7.1 and 2.2 kb transcripts). In addition, at least three other minor bands with a size of 6.8 kb, 6 kb, and 4.5 kb were observed. Since the 5' splice donor site of MoMLV was retained in pTEPN-G, these minor transcripts may arise from the use of this splice donor site and the downstream cryptic splice acceptor sites.

Upon 17β-estradiol induction, the level of the 7.1-kb genomic transcripts in the TEPN-G HT1080 cells increased approximately 4 fold whereas the level of the 2.2-kb transcript increased approximately 28 fold under the same conditions (as determined by densitometric analysis). Cell surface expression of VSV-G upon induction is thus correlated with an increase in transcription of the VSV-G gene from the tetO-containing promoter. These results demonstrate that cell lines containing genes encoding potential toxic gene products can readily be established with the inducible system described in this study, and the inducible system can be transferred into the host cell as a single construct.

These mRNA expression studies indicate that the effect of the LTR enhancer on the tetO-containing promoter in the TEPN-G construct, if any, is minimum. Thus there is little concern that the tetO-containing promoter in the retroviral construct may be activated fortuitously by the MoMLV LTR enhancer, which functions efficiently in many mammalian cell types. Minimal LTR-enhancer promoted transcription from inducible tetO promoter may be due to the fact that, except for the TATA box, the inducible tetO promoter contains no other regulatory elements from which LTR enhancer-activated transcription can occur. Transcriptional activation of the tetO-containing promoter by tTAER may be due to the close proximity of the tetO sites to the promoter.

Unexpectedly, the levels of mRNA initiated from the 5'LTR increased upon β-estradiol induction. The presence of putative estrogen-responsive elements in the MoMLV LTR may account for the observed increase. Alternatively, the strong transactivation domain of VP16 in tTAER may boost the LTR promoter activity upon binding of tTAER to the tetO sites.

Following procedures similar to those described above, other therapeutic proteins can be expressed from DNA inserted in the genome of an inner ear cell by gene transfer according to the invention.

The invention now being fully described, it will be apparent to one of ordinary skill in the art that many changes and modifications can be made thereto without departing from the spirit or scope of the appended claims.

What is claimed is:

1. A eukaryotic cell for packaging of a pseudotyped retroviral vector, the cell being derived from a Cf2Th cell, the cell comprising:

a stably chromosomally-integrated first nucleotide sequence encoding a retroviral Gag polypeptide;

a stably chromosomally-integrated second nucleotide sequence encoding a retroviral Pol polypeptide; and a third nucleotide sequence encoding a VSV G envelope protein operably linked to an inducible promoter, wherein transcription from the inducible promoter is regulated by a multi-chimeric transactivator comprising a) a first ligand-binding domain, wherein binding of a first ligand to the first ligand-binding domain inhibits transcriptional activation by the multi-chimeric transactivator;

b) a eukaryotic transcriptional activation domain; and c) a second ligand-binding domain;

wherein upon introduction of a retroviral RNA genome into the packaging cell and induction of expression from the inducible promoter, the packaging cell produces infectious retroviral viral particles at a titer of at least about $10^3$ cfu per ml within a period of about 2 days.

2. The eukaryotic cell of claim 1, wherein the eukaryotic transcription activation domain is a transcriptional activation domain of VP16.

3. The eukaryotic cell of claim 1, wherein the first ligand-binding domain is a tetracycline repressor polypeptide domain and the second ligand-binding domain is a ligand-binding domain of a steroid receptor.

4. The eukaryotic cell of claim 3, wherein the steroid receptor is an estrogen receptor.

5. The cell of claim 1, wherein the cell is further characterized by retrovital virion production of at least about $10^4$ infectious particles per ml per hour.

6. The cell of claim 1, wherein the cell can be maintained in in vitro culture while producing infectious retroviral particles for at least 7 days at a titer of at least about $10^5$ cfu per ml.

7. The eukaryotic cell of claim 1, wherein the cell further comprises a fourth nucleotide sequence encoding the multi-chimeric transactivator.

8. A method of producing a recombinant retroviral vector particle, the method comprising the steps of:

introducing into a eukaryotic cell derived from a Cf2Th cell a) a first nucleotide sequence encoding a retroviral Gag protein, b) a second nucleotide sequence encoding a retroviral Pol protein, c) a third nucleotide sequence encoding a VSV G envelope protein, said third nucleotide sequence being operably linked to an inducible promoter, and d) a fourth nucleotide sequence encoding a multi-chimeric transactivator comprising i) a first ligand-binding domain, wherein binding of a first ligand to the first ligand-binding domain inhibits transcriptional activation by the multi-chimeric transactivator;

ii) a eukaryotic transcriptional activation domain; and iii) a second ligand-binding domain;

introducing into the cell a recombinant retroviral genome for inclusion in a pseudotyped retroviral particle; and exposing the cell to conditions under which the multi-chimeric transactivator facilitates transcription from the inducible promoter;

wherein expression of the first, second, and third nucleotide sequences results in expression of the Gag, Pol, and VSV G envelope proteins, respectively, thereby resulting in packaging of the recombinant retroviral genome and production of pseudotyped retroviral particles at a viral titer of at least $10^3$ cfu per ml within a period of about 2 days.

9. The method of claim 8, wherein the first ligand-binding domain is a tetracycline repressor polypeptide domain and the second ligand-binding domain is a ligand-binding domain of a steroid receptor.

10. The method of claim 9, wherein the eukaryotic transcription activation domain of the multi-chimeric transactivator is a transcriptional activation domain of VP16, and the steroid receptor is an estrogen receptor.

11. The method of claim 8, wherein expression of the Gag and Pol proteins is constitutive.

12. A eukaryotic cell derived from a Cf2Th cell, the cell comprising:

a stably chromosomally-integrated first nucleotide sequence encoding a retroviral Gag polypeptide;

a stably chromosomally-integrated second nucleotide sequence encoding a retroviral Pol polypeptide;

a third nucleotide sequence encoding a VSV G envelope protein operably linked to an inducible promoter, wherein transcription from the inducible promoter is regulated by a multi-chimeric transactivator comprising i) a tetracycline repressor polypeptide domain;

ii) a eukaryotic transcriptional activation domain; and iii) a ligand-binding domain of a steroid receptor; and a retroviral genome comprising a packaging signal;

wherein upon induction of expression from the inducible promoter, the packaging cell produces infectious retroviral viral particles at a liter of at least about $10^3$ cfu per ml within a period of about 2 days.

13. The eukaryotic cell of claim 12, wherein the eukaryotic transcription activation domain is a transcriptional activation domain of VP16.

14. The eukaryotic cell of claim 13, wherein the steroid receptor is an estrogen receptor.

15. The cell of claim 12, wherein the cell is further characterized by retroviral virion production of at least about $10^4$ infectious particles per ml per hour.

16. The cell of claim 12, wherein the cell can be maintained in in vitro culture while producing infectious retroviral particles for at least 7 days at a titer of at least about $10^5$ cfu per ml.

* * * * *